(12) United States Patent
Marietta

(10) Patent No.: US 8,100,912 B2
(45) Date of Patent: Jan. 24, 2012

(54) SURGICAL SAGITTAL SAW WITH QUICK RELEASE INDEXING HEAD AND LOW BLADE-SLAP COUPLING ASSEMBLY

(75) Inventor: Joe Marietta, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 736 days.

(21) Appl. No.: 11/482,279

(22) Filed: Jul. 7, 2006

(65) Prior Publication Data

US 2007/0016238 A1    Jan. 18, 2007

Related U.S. Application Data

(60) Provisional application No. 60/699,315, filed on Jul. 14, 2005.

(51) Int. Cl.
| | |
|---|---|
| *A61B 17/00* | (2006.01) |
| *A61B 17/14* | (2006.01) |
| *A61B 17/32* | (2006.01) |
| *B26B 1/00* | (2006.01) |
| *B23D 45/00* | (2006.01) |
| *B27B 5/29* | (2006.01) |
| *B27B 19/09* | (2006.01) |
| *B27B 23/00* | (2006.01) |
| *B27B 33/20* | (2006.01) |

(52) U.S. Cl. ............ 606/82; 606/176; 30/338; 30/166.3
(58) Field of Classification Search .................. 606/79, 606/82, 176; 30/166.3, 338
See application file for complete search history.

(56) References Cited

U.S. PATENT DOCUMENTS

| | | | | |
|---|---|---|---|---|
| 1,327,026 A | * | 1/1920 | Dabbs et al. | 384/581 |
| 3,943,934 A | | 3/1976 | Bent | |
| 4,528,753 A | * | 7/1985 | Kuhlmann et al. | 30/392 |
| 5,263,972 A | * | 11/1993 | Evans et al. | 606/176 |
| 5,439,472 A | | 8/1995 | Evans | |
| 5,489,285 A | | 2/1996 | Goris | |
| 5,697,158 A | * | 12/1997 | Klinzing et al. | 30/166.3 |
| 7,204,026 B2 | * | 4/2007 | Phillips et al. | 30/394 |
| 2002/0198556 A1 | | 12/2002 | Ark et al. | |

FOREIGN PATENT DOCUMENTS

WO    WO 97/22303    6/1997

OTHER PUBLICATIONS

PCT Appp. No. PCT/US2006/026410, ISA Srch Rpt. & Wrtn Opn Dec. 12, 2006.
Stryker Corporation, System 5 Sagittal Saw Sep. 2002, 3 pages.
Hall Power Pro Sagittal Saw, Jan. 2004, 2 photographs.

* cited by examiner

*Primary Examiner* — Thomas Barrett
*Assistant Examiner* — David W Bates

(57) ABSTRACT

A surgical sagittal saw with a head that is able to index, rotate, relative to the longitudinal axis of the saw housing. The head has a neck that extends into an open distal end of the housing. A biasing assembly holds the head and neck sub-assembly in the open distal end of the housing. The biasing assembly is rotatable relative to the housing. A separate lock mechanism selectively holds the head in a fixed orientation around the saw housing longitudinal axis.

30 Claims, 16 Drawing Sheets

SURGICAL SAGITTAL SAW WITH QUICK RELEASE INDEXING HEAD AND LOW BLADE-SLAP COUPLING ASSEMBLY

RELATIONSHIP TO EARLIER FIELD APPLICATION

This application claims priority under 35 U.S.C. Sec. 119 from U.S. Patent Application No. 60/699,315 filed 14 Jul. 2005.

FIELD OF THE INVENTION

This invention relates generally to a surgical sagittal saw. More particularly, this invention relates to a surgical sagittal saw with an indexing head that is easy to rotate and a coupling assembly for receiving a saw blade that minimizes the post insertion movement of the blade in the coupling assembly.

BACKGROUND OF THE INVENTION

The powered saw is an important powered tool that a surgeon employs to perform certain surgical procedures. A typical powered saw has a handpiece in which is housed either an electrically or pneumatically driven motor. The motor is attached, through a drive shaft, to a head. The head is designed to removably receive a saw blade. Actuation of the motor causes movement of the saw blade. This movement of the saw blade gives the blade the power to cut through the tissue it is employed to separate. Powered surgical saws are able to cut through both hard and soft tissue much faster, and with greater accuracy, than the manually operated saws that they have replaced. Also, it should be clear that the physical effort a surgeon has to employ to operate a powered surgical saw is much less than that used when cutting tissue with manual saws.

Some surgical saws are designed for use with flat saw blades. Typically, this type of saw blade has a base that seats in a complementary slot or opening formed in the head. The base of the blade has one or more openings or slots in which coupling members integral with the saw head seat in order to lock the blade to the head. Extending from the base, the saw blade has a main body. The leading edge of the main body is formed with teeth that perform the cutting action.

Many surgical saws are designed so that their heads and complementary blades engage in a repetitive right-left-right-left oscillating motion. More specifically, the head of an oscillating motion saw moves in either sagittally or reciprocates. When a blade is moved sagittally, it pivots in a plane parallel to the longitudinal axis of the saw head. When a blade reciprocates it moves back and forth along the longitudinal axis of the blade.

Over the past few years, it has become popular to provide powered surgical sagittal saws with heads that have tooless mechanisms for coupling the saw blades to the saws. These mechanisms often have a spring loaded device for holding the head coupling members in position that lock the saw blades in place. The coupling member is displaced from the locked state to the load state by the depression of a button also built into the saw head. One advantage of these assemblies is that they make replacing saw blades, which can occur during surgery, a relatively simple task. All one has to do is depress the button in order to move the coupling member to the unlocked state; the surgical personnel then remove one blade and insert a new blade. Still another advantage of these assemblies is that they eliminate the need to bring another tool, either a small wrench or a key, into the surgical suite. The elimination of this tool eliminates the need to have to sterilize it before an operation and the need to have to account for its presence.

While current surgical saws, with tooless heads, have proven to be useful surgical tools, there is a disadvantage associated with their use. When an oscillating motion saw with this type of head is actuated, it generates a significant amount of noise. This is because current saw blades do not tightly fit into the saw head slots in which they seat. There are two reasons for this. First, these saw heads and their complementary blades are inherently dimensioned so that there is a small interstitial gap between the blade and the adjacent walls of the saw head that define the complementary slot. This gap ensures the base of the blade can be quickly slide into and removed from the slot. Secondly, there is a slight gap due to the inherent manufacturing tolerances that arise during fabrication of these components. Consequently, each time a saw head changes its direction of motion, the inertial movement of the saw blade, which is still traveling in the first direction, causes the side of the blade to abut, slap, against the adjacent surface of the saw head. Each time this motion occurs, noise is produced. These saw blades typically oscillate back-and-forth at a rate of 10,000 to 20,000 cycles/min. The cumulative noise produced by the saw blade repetitively striking the interior walls of the saw head in which it is seated is quite noticeable.

There have been attempts to provide saw head-and-blade assemblies designed to minimize the noise produced when these components are actuated. In one such assembly, the saw head is provided with tapered pins and the base of the saw blade is provided with holes in which the pins seat. This arrangement is intended to provide a tight fit between the pins and the adjacent section of the saw blade through which the pins seat. By providing this tight fit, the post-insertion play of the saw blade is reduced. The reduction in this play reduces the incidence of the blade striking the interior walls of the saw head and the noise generated by such action. This assembly has minimized the noise associated with the actuation of a surgical saw. However, it is costly to precision machine the tapered pins used to hold the saw blade in the head.

Moreover, often a sagittal saw will include an indexing mechanism. The indexing mechanism rotates the saw head so the saw blade is in a specific angular orientation relative to a center axis that extends through the saw. The indexing mechanism makes it possible for the surgeon to best position the saw blade to accomplish the desired surgical task.

A number of known indexing mechanisms include a neck-in-collar arrangement. Thus, a neck integral with the saw head is rotatably fitted in a collar integral with the static housing of the saw. One disadvantage of known indexing mechanisms is that, for the saw head and neck to be rotated, the surgical personnel must employ a significant amount of manual force to overcome the retention mechanism used to hold the head and neck to the rest of the handpiece. Still another disadvantage of known indexing assemblies is that, over time, a corrosive bond may form between the fixed collar and the rotating neck. The formation of this bond can be accelerated by the moisture to which the saw is exposed when sterilized. When such bonding occurs, it becomes increasingly difficult to use manual force to index the saw head and neck relative to the static collar.

Also, a locking tab is normally employed in an indexing mechanism to prevent the axial rotation of the sagittal head. Known tabs loosely fit in the slots in which they are seated. This loose fit causes the tab to vibrate against the surface of the adjacent slot-defining surfaces. This contact adds to the noise produced when the saw is actuated.

SUMMARY OF THE INVENTION

This invention is related to a new and useful surgical sagittal saw. The surgical sagittal saw of this invention has an indexing head that is relatively easy to rotate, index. The surgical sagittal saw of this invention also has a coupling assembly that snuggly holds the blade fitted to the coupling assembly in place.

Specifically, the surgical sagittal saw of this invention includes a head and a neck subassembly. The neck is rotatably fitted in a static front collar. Ball bearings facilitate rotation of the neck relative to the front collar. A retention assembly holds the head and neck assembly to the front collar. A locking assembly separate from the retention assembly holds the neck in a fixed rotational position relative to the front collar.

A blade mount is rotatingly fitted in the head. The blade mount includes a blade slot for receiving the proximal rear end of the blade. Interior side walls of the blade mount that define the blade slot taper inwardly. The blade mount has a member for holding the blade in the blade slot. There is also a mechanism for selectively urging the blade against the opposed tapered sidewalls.

BRIEF DESCRIPTION OF THE DRAWINGS

The invention is pointed out with particularity in the claims. The above and further advantages of the invention may be better understood by reference to the following detailed description of a preferred embodiment of the invention when taken in conjunction with the accompanying drawings, in which:

DETAILED DESCRIPTION

Figure 1:
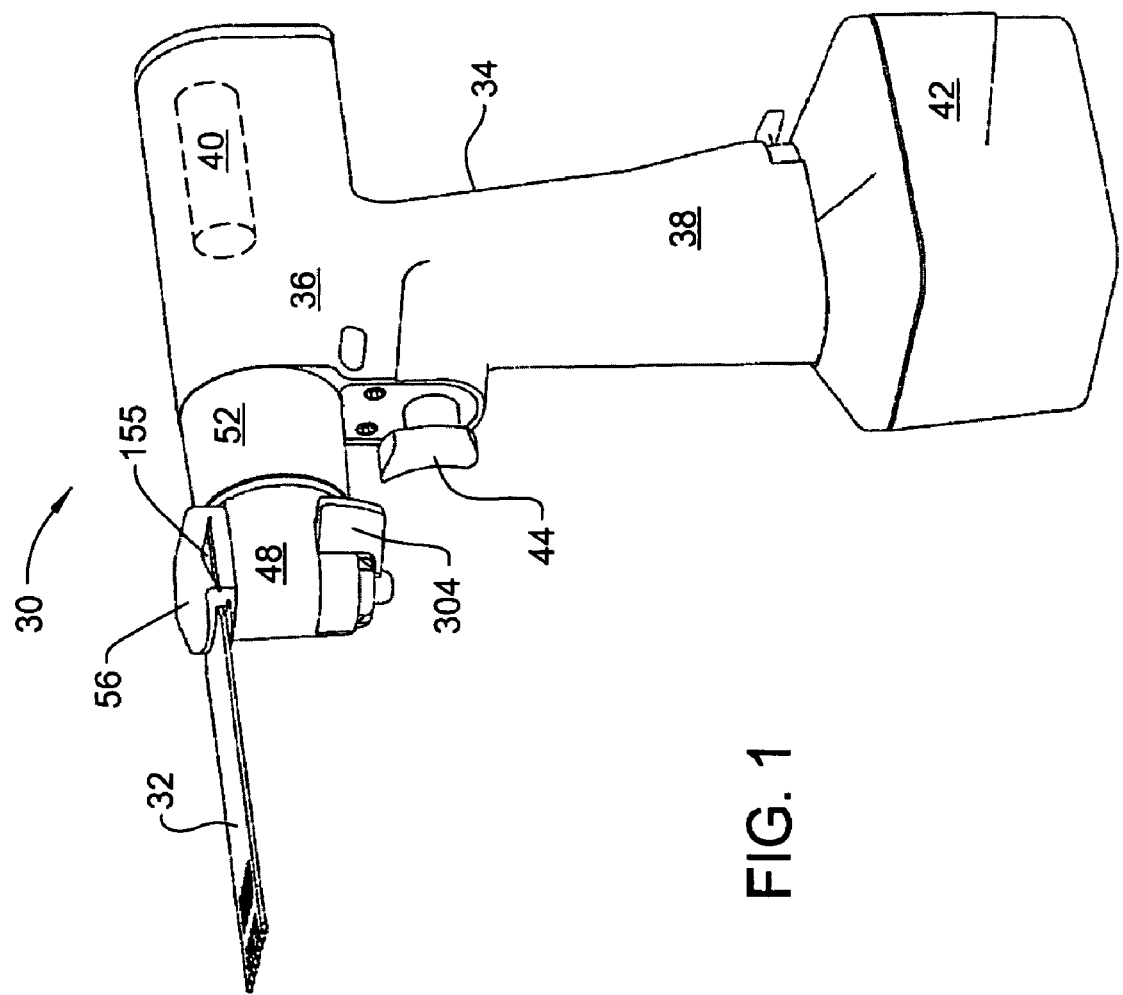
FIG. 1 is a perspective view of a surgical sagittal saw constructed in accordance with this invention.
Figure 2:
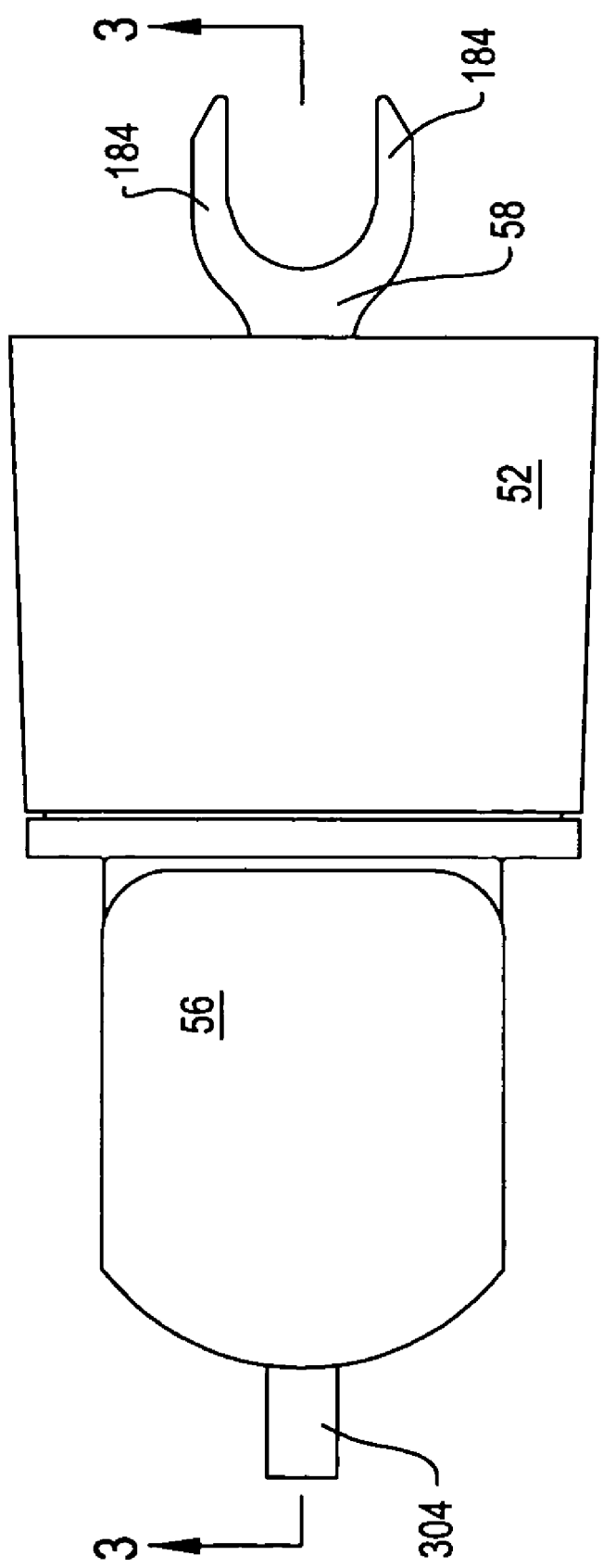
FIG. 2 is a top view of the saw head of this invention.

FIG. 1 illustrates a surgical sagittal saw 30 constructed in accordance with this invention for oscillating a saw blade 32. Saw 30 includes a housing 34. In the particular version of the invention, housing 34 is shaped to have a generally barrel shaped head 36. A pistol-grip shaped handle 38, also part of housing 34, extends downwardly from head 36. A motor, represented by a phantom cylinder 40, is disposed inside housing head 36. In some versions of the invention, the motor is a brushless DC motor. It should be appreciated that this is exemplary, not limiting. In other versions of the invention, the motor may be a DC motor with brushes, an AC driven motor or a motor that is pneumatically or hydraulically driven. In the illustrated version of the invention, saw 30 is cordless tool. A battery 42 removably attached to the butt end of the handle 38 contains a charge for energizing the motor. Again, it should be understood that the invention is not so limited. In alternative versions of the invention, a power cord, an air line or a fluid line is connected to the housing 34 for providing the power needed to actuate the motor.

A trigger 44 is moveably mounted to the saw housing 34. In the illustrated version of the invention, trigger 44 extends distally forward from the handle 38 immediately below the head 36. ("Distal", it shall be understood means toward the surgical site to which the handpiece 30 is directed. "Proximal", means away from the surgical site.). A control circuit internal to the housing 34, not illustrated and not part of this invention, monitors the actuation of the trigger 44. Based on the extent to which the trigger switch 44 is actuated, the control circuit selectively energizes the motor to cause an output shaft integral with the motor to rotate at the desired speed.

The basic structure of distal front end components of saw 30 of this invention is now explained by reference to FIGS. 2-5. A sagittal head 48 is positioned distally forward of the saw housing head 36. A sagittal neck 50, seen in FIG. 5, is integrally attached to and extends proximally rearward from the sagittal head 48. The sagittal neck 50 is fitted in a front collar 52 that extends distally forward from housing head 36. Neck 50 is mounted in collar 52 so as to be able to rotate around the longitudinal axis of the collar. A lock assembly 54 holds the sagittal neck 50 and head 48 in a fixed position relative to the front collar 52 and, more particularly along the longitudinal axis of the collar.

Figure 3:
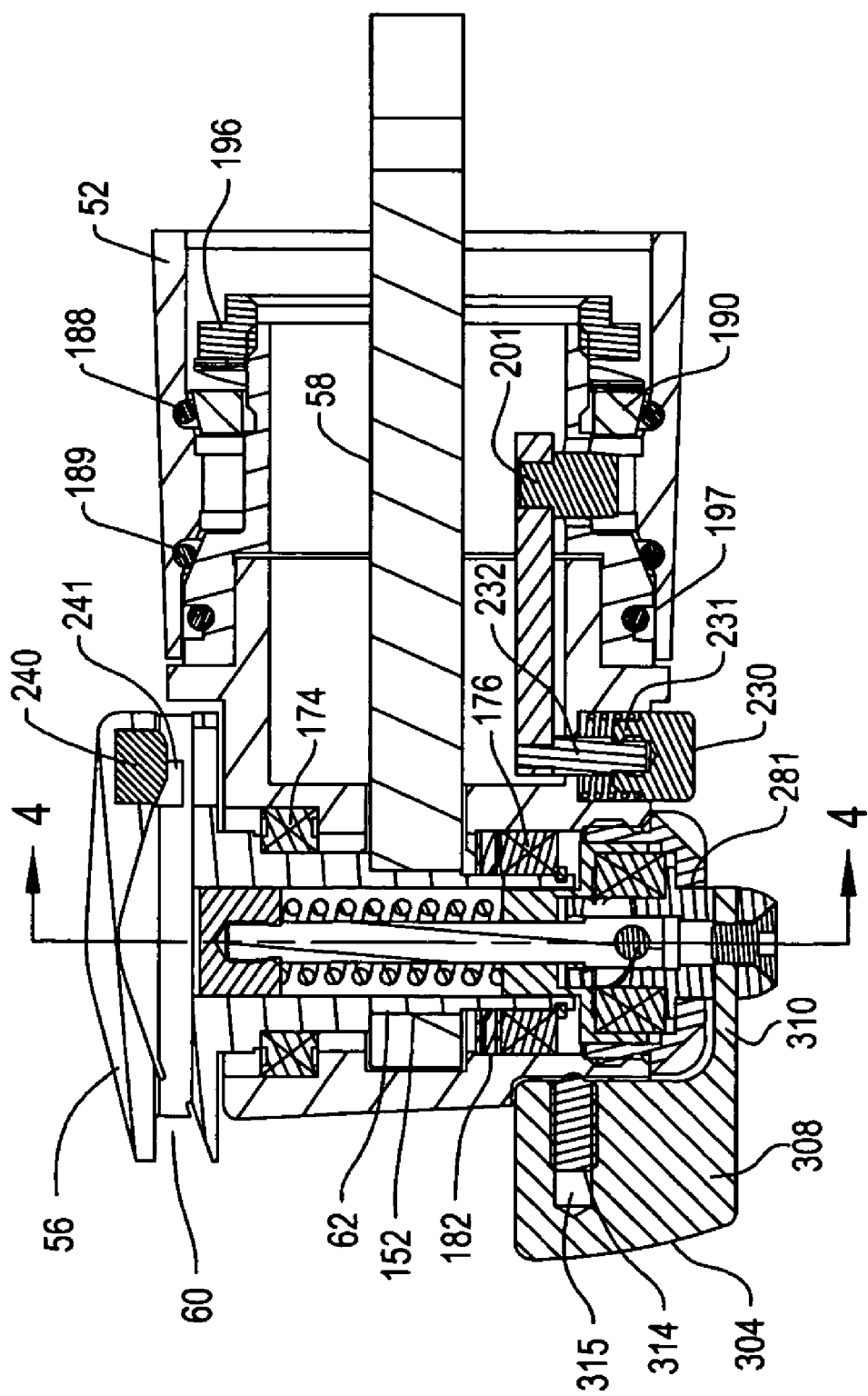
FIG. 3 is a cross sectional view of the saw head taken along line 3-3 of FIG. 2.
Figure 4:
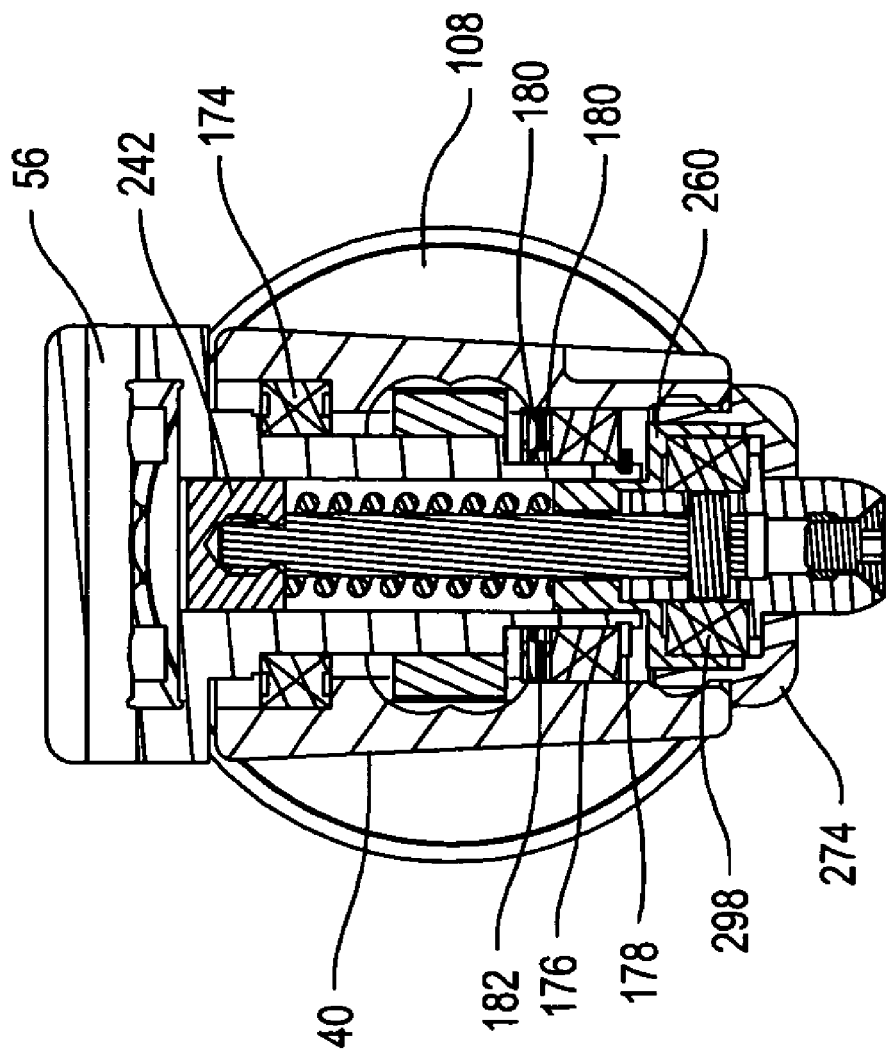
FIG. 4 is a cross sectional view of the saw head taken along line 4-4 of FIG. 3.
Figure 5:
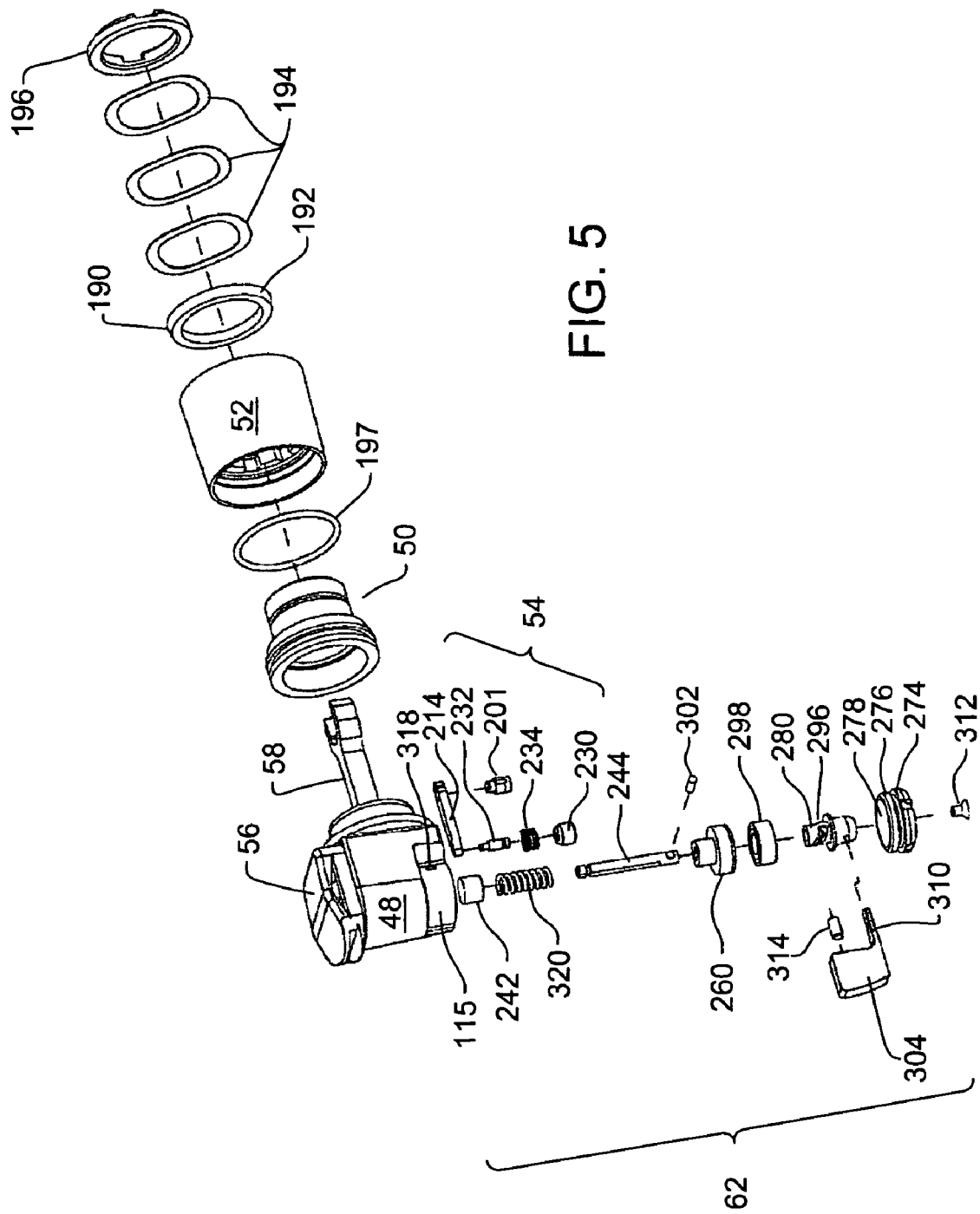
FIG. 5 is an exploded view of the saw head.

A blade mount 56, seen in FIGS. 3 and 4, is rotating fitted in the sagittal head 48. A drive assembly, represented by a drive link 58 (FIGS. 2 and 5), oscillates the blade mount 56 back and forth around the longitudinal axis of the blade mount. Blade mount 56 includes a blade slot 60 for receiving the proximal end of the saw blade. A retention assembly 62 holds the blade 32 in the blade slot 60.

Figure 8:
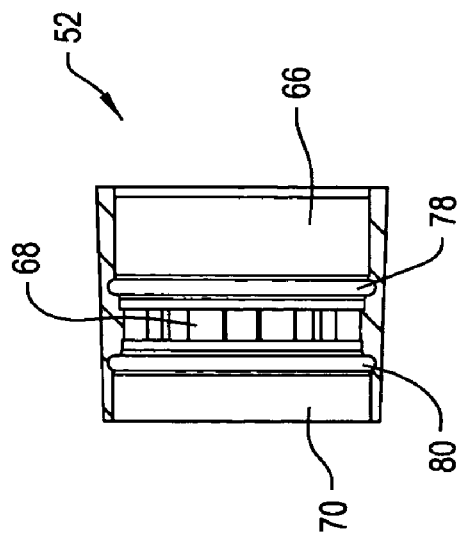
FIG. 8 is a cross sectional view of the collar taken along line 8-8 of FIG. 7.
Figure 7:
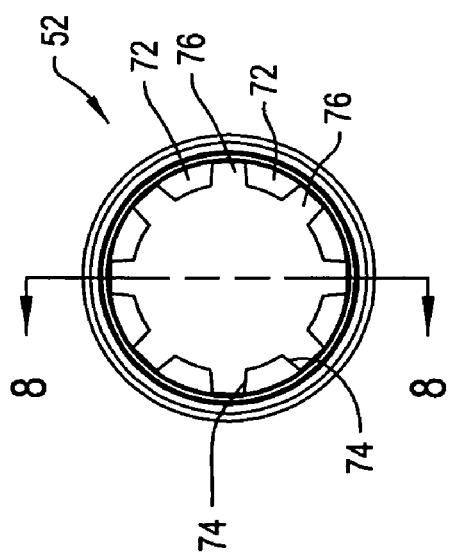
FIG. 7 is view looking into the collar.
Figure 6:
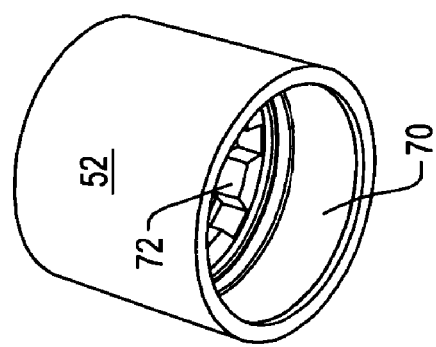
FIG. 6 is a perspective view of the front collar of the saw of this invention.

The structure of the saw front collar 52 is now described by reference to FIGS. 6-8. The collar 52 is shaped to have an outer diameter that tapers inwardly from the proximal to the distal ends of the collar. Collar 52 is further shaped to have a number of different coaxial bore sections that collectively form a through opening through the collar. A proximal bore section 66 extends forward from the proximal end of the collar 52. A middle bore section 68 is contiguous with and extends distally forward from the proximal bore section 66. Middle bore section 68 has a diameter less than that of proximal bore section 66. A distal bore section 70, contiguous with middle bore section 68, forms the distal end opening of the collar 52. Distal bore section 70, in the illustrated version of the invention has a diameter greater than that of the proximal bore section 66.

Collar 52 is further formed to have a number of arcuately spaced apart tabs 72 that project inwardly from the inner wall that defines middle bore section 68. Each tab 72 has two side faces 74, which are angled inwardly toward each other. Located between each tab 72 is a slot 76. Owing to the angled orientation of side faces 74, each slot 76 has a lateral cross sectional profile that outwardly increases relative to the distance from the inner wall of the collar 52.

The collar 52 is also shaped to define two interior circumferential grooves 78 and 80. Groove 78 is located at the distally located base of proximal bore section 66, immediately rearward to the collar inner wall that defines middle bore section 68. Groove 80 is located at the proximally located base of distal bore section 70, immediately forward to the collar inner wall that defines middle bore section 68.

Collar 52 is fitted to the saw housing head 36 by press fitting. Sometimes, the collar 52 is attached to an adaptor (not illustrated) that extends forward from a distal facing opening in the housing head 36.

Figure 11:
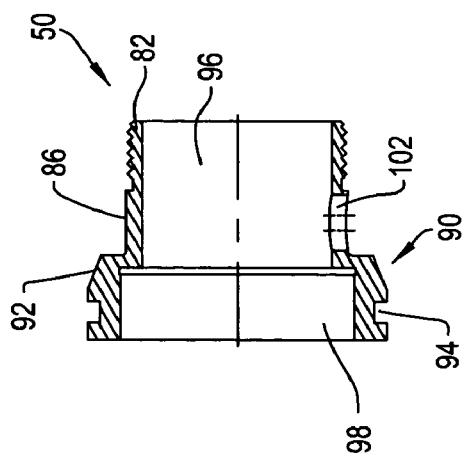
FIG. 11 is a cross sectional view of the sagittal neck taken along line 11-11 of FIG. 10.
Figure 10:
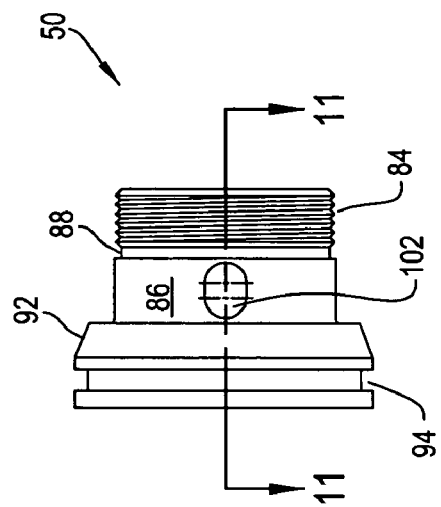
FIG. 10 is a plan view of the bottom of the sagittal neck.
Figure 9:
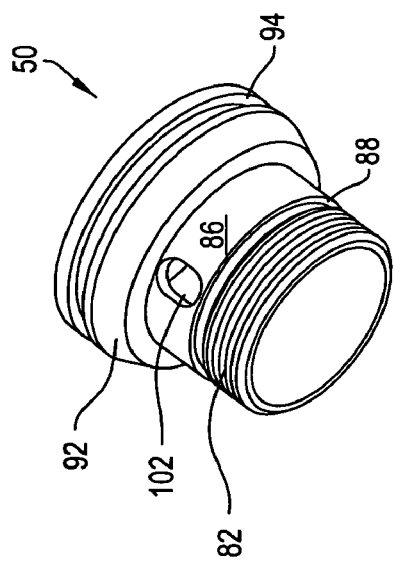
FIG. 9 is a perspective view of the sagittal neck.
Figure 15:
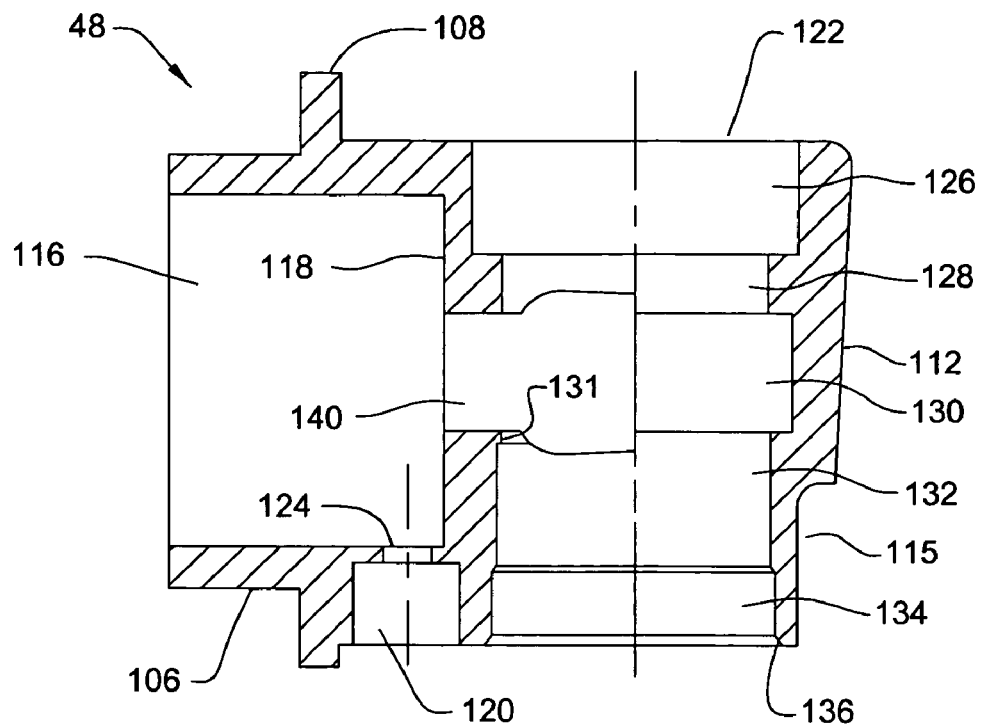
FIG. 15 is a cross sectional view of the sagittal neck taken along line 15-15 of FIG. 14.
Figure 12:
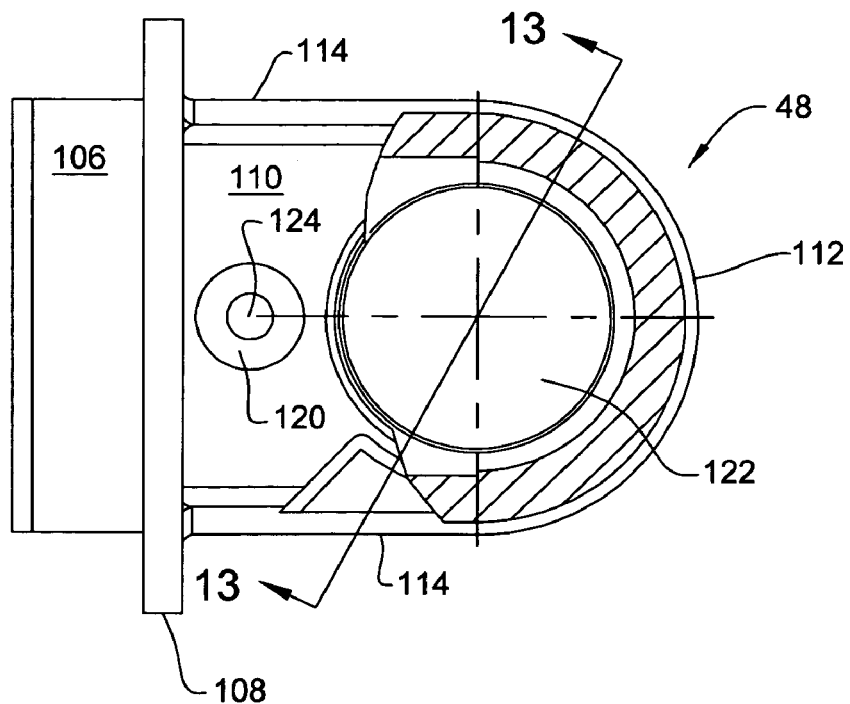
FIG. 12 is a top plan view and partial cutaway view of the sagittal head.
Figure 14:
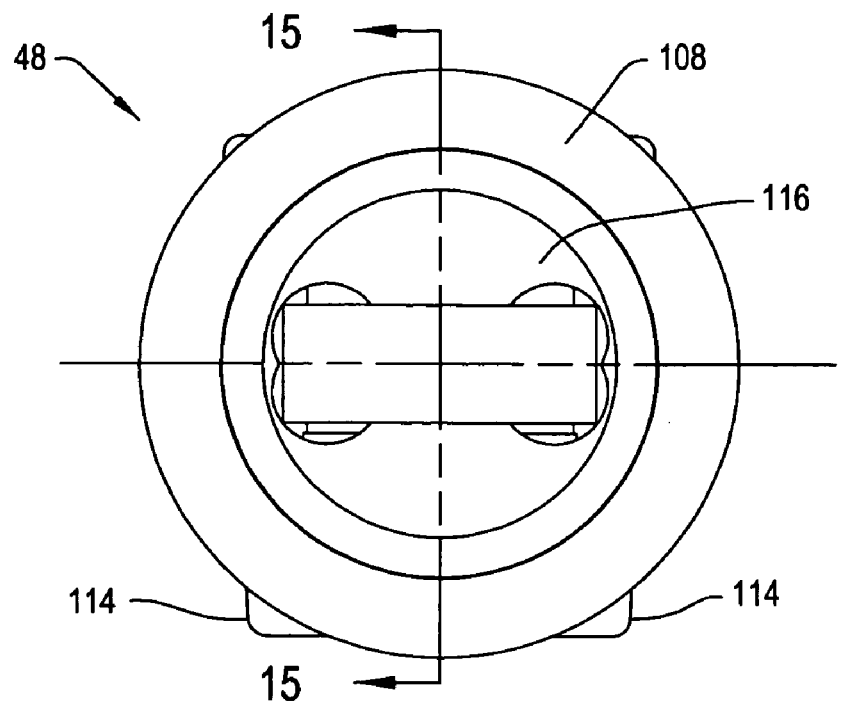
FIG. 14 is a plan view, looking distal forward, of the proximal end of the sagittal neck.
Figure 13:
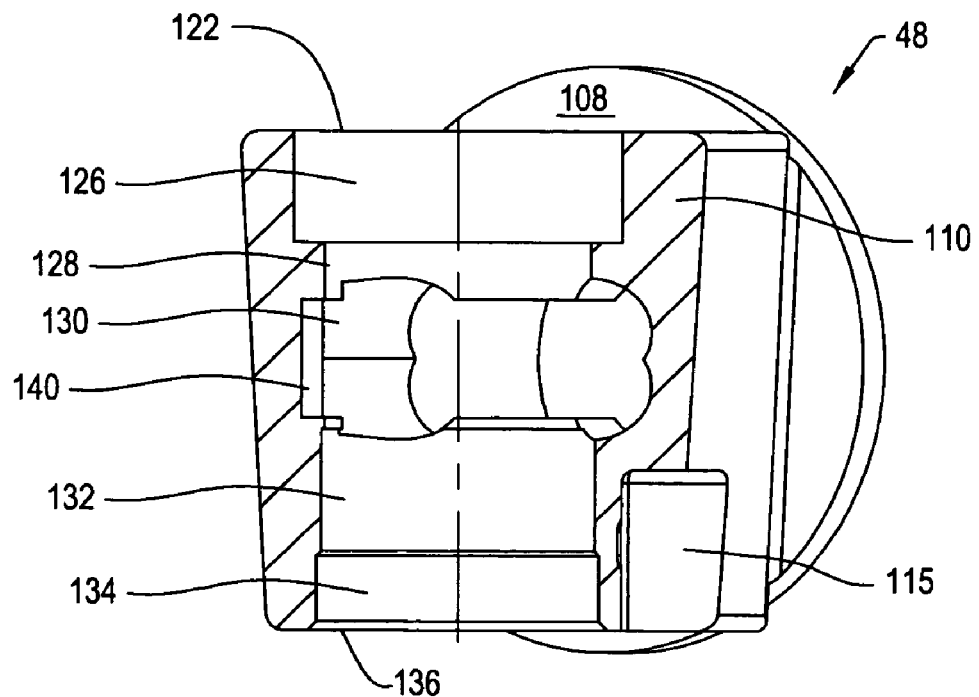
FIG. 13 is a cross sectional view of the sagittal neck taken along line 13-13 of FIG. 12.

The sagittal neck 50, now described by reference to FIGS. 9-11, is formed from a single piece of metal and is generally tubular in shape. Sagittal neck 50 includes a proximally located stem 82. The outer surface of neck stem 82 is provided with threading 84. Distally forward of stem 82, sagittal neck 50 has an intermediate section 86. The intermediate section 86 has a constant outer diameter greater than the diameter of stem 82. An undercut 88 is located between stem threading 84 and intermediate section 86 for manufacturing reasons.

The sagittal neck 50 is further shaped to have a distal-located forward section 90 immediately in front of intermediate section 86. Forward section 90 has an outer diameter greater than that of intermediate section 86. More particularly, the neck forward section 90 is shaped so that, immediately forward of the step surface between the intermediate and forward sections 86 and 90, respectively, to have a tapered outer surface 92. Outer surface 92 tapers outwardly as the surface extends distally forward along the length of the neck 50. Thus, relative to axis extending through collar 52, outer surface 92 is at angle less than a right angle. Forward of outer surface 92, the neck forward section 90 is shaped to have an outer surface with a constant diameter. An annular groove 94 is formed in the neck forward section 90 to extend inwardly of outer surface 92.

Two axially contiguous bores 96 and 98 collectively define the longitudinal through opening in the sagittal neck 50. Bore 96 extends forward from the proximal end of the neck 50 through stem 82 and intermediate section 86. Bore 98 extends from the distal end of bore 96 through the neck forward section 90. The sagittal neck 50 is further formed to have an opening 102 in the intermediate section 86. Opening 102 extends laterally through the neck intermediate section 86 into bore 96. In the illustrated version of the invention, opening 102 has an oval cross-sectional profile.

The sagittal head 48, seen in FIGS. 12-15, is also formed from a single piece of metal. The most proximal portion of sagittal head 48 is a circular base 106. Base 106 has an outer diameter that facilitates the press fitting of the base in the sagittal neck distal end bore 98. Forward of base 106, the sagittal head 48 is formed to have a circular outer flange 108. Flange 108 projects outwardly beyond base 106. When the sagittal head 48 is press fit to the sagittal neck 50, flange 108 abuts the front face of neck 50 to limit the insertion.

A front section 110 extends forward of flange 108 and is the most distal portion of sagittal head 48. Front section 110 has a front surface 112 that, when viewed from the top or bottom, has a curved profile. Opposed side surfaces 114 extend forward from flange 108 to front surface 112.

Sagittal head 48 is further shaped to define a recess 115. Recess 115 is located around the bottom of the head 48 and extends inwardly from the front surface 112 and has a base (not identified) that subtends an arc of approximately 120°.

The sagittal head 48 is formed with a number of bores and openings. A proximal end bore 116 extends axially forward through base 106 beyond flange 108 and partially into front section 110. Bore 116 is a closed end bore; the bore terminates at an interior wall 118 within sagittal head 48.

Sagittal head front section 110 is formed with two parallel bores 120 and 122. Bores 120 and 122 are aligned on axes perpendicular to the longitudinal axis of proximal end bore 116. Bore 120 is the more proximal and small diameter of the two bores. Bore 120 opens from the bottom surface of sagittal head front section 110 and is directed towards the distal front end of proximal end bore 116. Bore 120 is a closed end bore. However, an opening 124 formed in the inner wall of the sagittal head 48 that defines the base of bore 120, coaxial with bore 120, extends into proximal end bore 116.

Bore 122 has coaxial sections with different diameters and extends through the sagittal head front section 110, top to bottom. There is a bore first section 126 that opens downwardly from the top surface of the sagittal head front section 110. Bore first section 126 opens into a bore second section 128. The bore second section 128 has a diameter less than that of the bore first section 126. A bore third section 130 opens downwardly from the bore second section 128. Bore third section 130 has a diameter approximately equal to that of the bore first section 126.

The bore third section 130 opens into a bore fourth section 132. The bore fourth section 132 has a diameter equal to that of the bore second section 128. In between bore third and fourth sections 130 and 132, respectively, the sagittal head 48 is formed to have inwardly extending circumferential lip 131. The through opening through lip 131 has a diameter less than that of the bore fourth section 132. A bore fifth section 134 is the bottommost section of bore 122 and opens into the bottom surface of the sagittal head front section 110. The bore fifth section 134 has a diameter between those of the bore third and fourth sections 130 and 132, respectively. The inner circular surface of the sagittal head 48 that defines the bore fifth section 134 is provided with threading (not illustrated). A small tapered counterbore 136 surrounds the open end of bore fifth section 134.

The sagittal head is further formed with an opening 140 that extends between the base of proximal end bore and the third section 130 of bore 122. Opening 140 has a rectangular cross sectional profile. Pocket-defining ledges (not identified) are formed in bore sections 128, 130 and 132 adjacent opening 140. These pockets facilitate the assembly/disassembly of components in the sagittal head 48.

Figure 17:
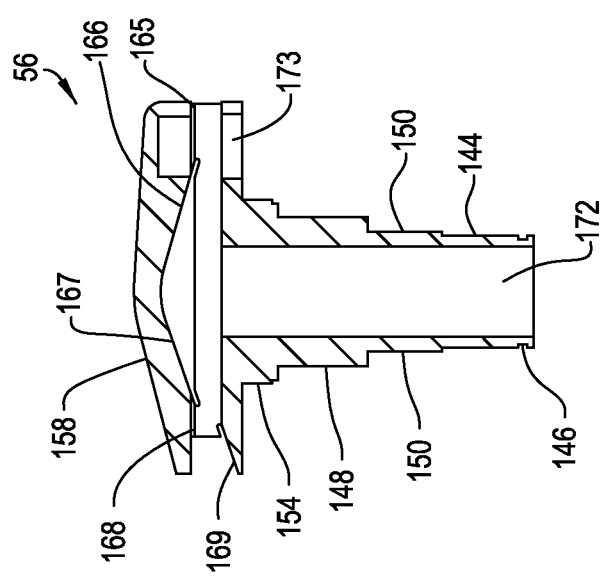
FIG. 17 is a cross sectional view of the blade mount.
Figure 16:
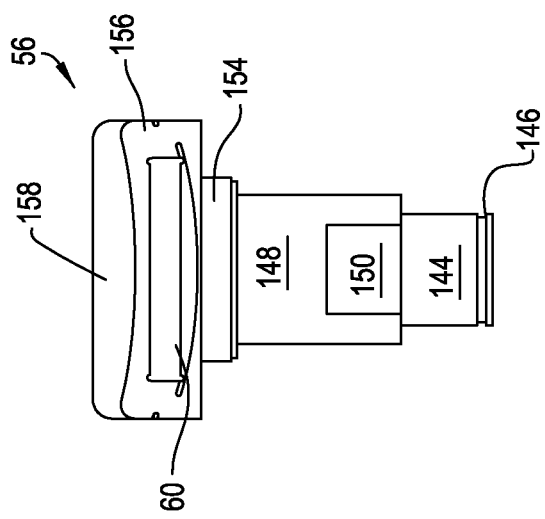
FIG. 16 is a plan view of the distally facing front of the blade mount.
Figure 18:
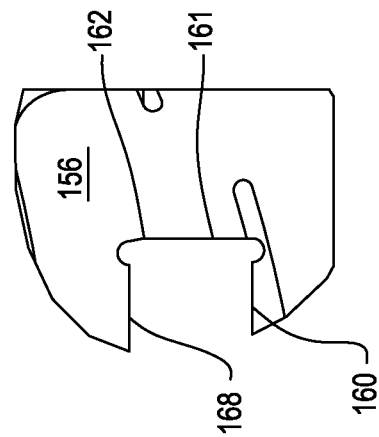
FIG. 18 is an enlarged plan view of the head geometry that defines the blade slot internal to the blade mount.

FIGS. 16-18 illustrate the blade mount 56 which is similarly formed from a single piece of metal. Starting at the bottom, the blade mount 56 is formed to have a cylindrical stem 144. An annular groove 146 extends inwardly around the outer surface of stem 146. Groove 146 is located immediately above the bottom end of the stem 144. Located immediately above the stem 144, the blade mount 56 is formed to have a generally cylindrical trunk 148. Trunk 148 has an outer diameter greater than that of the stem 144. While the trunk 148 has a generally circular cross sectional profile, the trunk is formed to have two diametrically opposed flats 150. When saw 30 of this invention is assembled, trunk flats 150 abut complementary faces that form a bore 152 in the distal end of the drive link 58 (FIG. 3). This arrangement causes the blade mount 56 to engage in a rotating oscillation in response to the pivotal oscillation of the drive link 58.

Blade mount 56 has a circular neck 154 located immediately above the trunk 148. The neck 154 has a diameter greater than that of the trunk 148. A generally rectangularly cross sectional shaped head 156, located immediately above the neck 154, forms the top section of the blade mount. Blade mount head 156 is shaped to subtend an area larger than that of the blade mount sections located below the head. A top surface 158 of the head 156 has at the distal end, a downwardly sloped surface. Blade mount head top surface 158 is so shaped to minimize the extent to which the blade mount obstructs the surgeon's forward view.

Figures 26A, 26B:
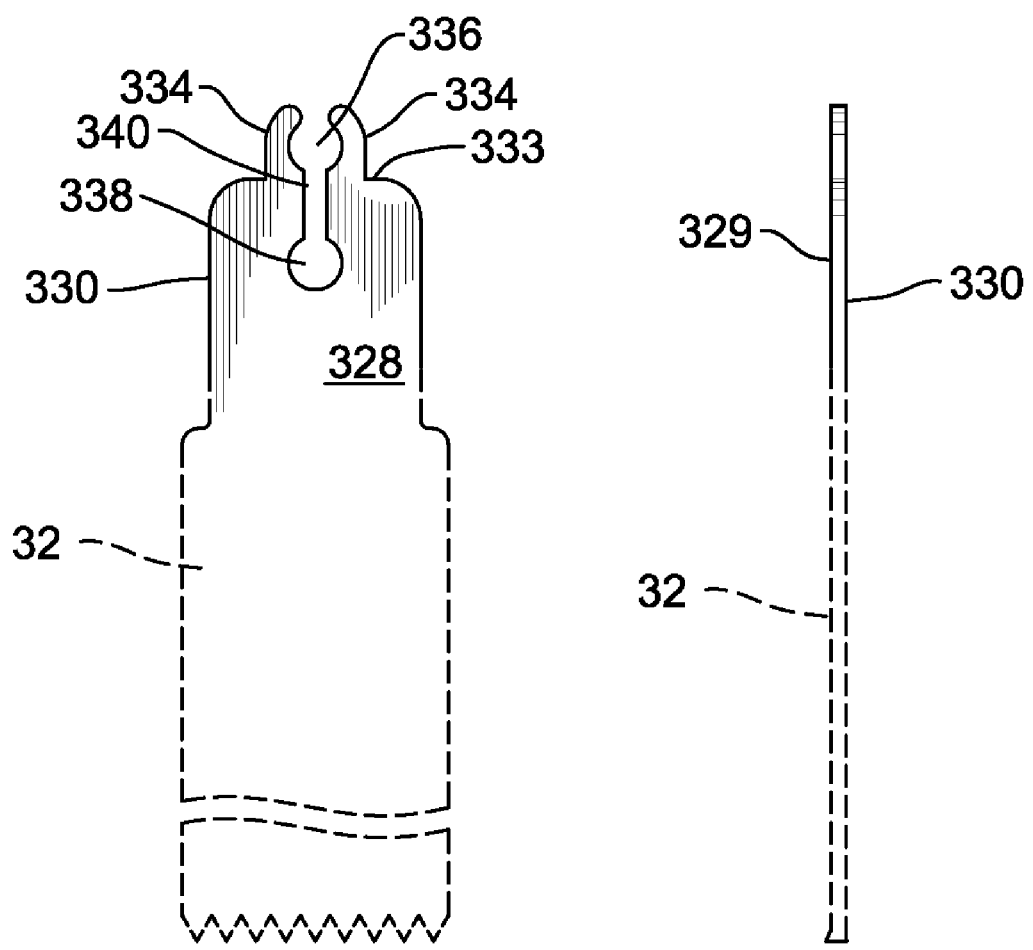
FIGS. 26A and 26B are, respectively, plan and side views of the proximal end of the saw blade, the end inserted in the blade mount.

The blade slot 60 is defined by a number of interior surfaces within the blade mount head 156. Generally, head 156 is shaped so that slot 60 extends completely through, front to back, the head. The blade slot 60 is defined, in part, by a bottom interior surface 160. The opposed side perimeters of slot 60 are each defined by two side interior surfaces, surfaces 161 and 162 (shown on one side of the slot 60 in FIG. 18). Specifically, opposed surfaces 161 extend perpendicularly upwardly from the ends of bottom interior surface 160. Surfaces 161 thus define a slot first section, (not identified). Surfaces 161 are thus parallel to each other. Surfaces 161 have a height that is slightly greater than the thickness of the proximal end of the associated saw blade 32. For example, in one version of the invention, surfaces 161 have a height that, at a minimum, is approximately 0.9 mm greater than the proximal end thickness of the associated blade, the side-to-side distance along the edges surfaces 329 of the saw blade (FIG. 26B). Blade mount head 156 is further shaped so that surfaces 161 define the slot first section so the slot section has a width slightly greater than the width across the face surfaces 328 (FIG. 26A) at the proximal end of the associated saw blade. For example, this distance may be approximately 0.03 mm greater than the width of the complementary blade 32. This sizing is to facilitate the easy insertion and removal of the saw blade to and from the slot.

Opposed interior side surfaces 162 of the blade mount head 156 taper inwardly relative towards each other define a slot second section, not identified. Specifically, blade slot 60 is shaped so that the width across top interior surfaces 165 and 168, the width of the top of the slot second section, is slightly less than width across the face surfaces 328 at the proximal end of the complementary saw blade 32. In some versions of the invention, the width across the top interior surfaces 165 and 168 that defines the blade slot 60 is approximately 0.09 mm less than the width of the complementary blade.

Blade mount base head 156 is further formed to have plural interior surfaces 165, 166, 167, 168 that define the top of the blade slot 60. Extending distally forward from the proximal end of head 156, there is surface 165. Surface 165 is parallel to the opposed bottom interior surface 160 that defines the base of the blade slot. Surface 165 extends over approximately one-fifth the length of the blade slot 60. Interior surface 166 borders and extends forward from surface 165. Surface 166 extends diagonally upwardly from the forward edge of surface 165. Surface 167 extends forward and diagonally downwardly from the distal forward end of surface 166. Collectively, surfaces 166 and 167 extend over approximately three-fifths the length of the blade slot 60. Surface 168 is the most distal interior surface of head 156 that defines the blade slot 60. Surface 168 extends forward from surface 167 and is coplanar with proximally located surface 165.

The blade mount head 156 is shaped so that surfaces 166 and 167 extend laterally across the head. Thus, end edges of surfaces 166 and 167 in combination with bottom interior surface 160 collectively define two triangularly shaped side windows 155 in the blade head (one shown in FIG. 1). Windows 155 facilitate access to the interior of the blade slot 60 for cleaning and sterilization.

Blade mount head 156 is further formed to define a lip 169 contiguous with the distal end of bottom interior surface 160. Lip 169 extends diagonally downwardly from the opening into blade slot 60.

Blade mount 56 is further formed to have a vertically extending bore 172. Bore 172 is a constant diameter bore that extends from the end of stem 144, through trunk 148, neck 154 and head 156. Bore 172 opens into bottom interior surface 160 that defined the base of the blade slot 60. The bore 172 is center over a line that defines the apex where top interior surfaces 166 and 167 meet. The blade mount head 156 is further formed to have a bore 173 located in a proximal section of the head. Bore 173 is a constant diameter bore that opens from the bottom of the blade mount head 156, intersects the blade slot 60 and extends into the top of the blade mount head. The portion of bore 173 that extends into upwardly from head interior surface 165 is close-ended. As discussed below, bores 172 and 173 house components forming the retention assembly 62 that hold the saw blade 32 in slot 60.

Returning to FIGS. 3 and 4, it can be seen that two bearing assemblies 174 and 176 rotatably secured the blade mount 56 in the sagittal head bore 122. A top located bearing assembly, bearing assembly 174 in FIG. 4, is seated on the annular step internal the sagittal head that defines the base of the first bore section 126. The inner race of bearing assembly 174 (race not illustrated) is disposed around the section of the blade mount trunk 148 immediately below the neck 154. The upwardly directed surface of the bearing assembly inner race seats against the annular stepped surface of the blade mount 56 that defines the transition from the trunk 148 to the neck 154 (annular surface not identified). The outer race of bearing assembly 174 is seated in the base of blade mount bore first section 126.

The lower of the two bearing assemblies, bearing assembly 176, extends between the curved inner surface of the sagittal head 48 that defines the bore fourth section 132 and the adjacent outer wall of the bearing mount stem 174. A retaining ring 178 snap fitted in the blade mount groove 146 holds the bearing assembly 176 in the sagittal head bore 120. Washers 180 and 182 hold bearing assembly 176 against retaining ring 178. Two washers 180 are provided. One washers 180 is located adjacent the downwardly facing annular surface of sagittal head lip 131. The second washer 180 is located over the upwardly facing surfaces of the races of bearing assembly 176 (races not illustrated). Washer 182 is a wave washer disposed between washers 180. The force exerted by wave washer 182 urges bearing assembly 176 against retaining ring 178. While not illustrated, it should be understood that, in some versions of the invention two or more washers 182 are provided.

Not shown and not part of this invention is the assembly internal to handpiece housing 34 that converts the rotary motion output from the motor into a motion able to oscillate drive link 58 back and forth. Generally, it should be understood that the proximal end of the drive link 58 is formed with two opposed fingers 184, seen in FIG. 2. Fingers 184 are spaced apart a sufficient distal to receive a bearing assembly (not illustrated). The bearing assembly is rotated in an excentric pattern by a drive shaft driven by the motor. An understanding of one such assembly is obtained from the Applicant's Assignee's U.S. patent application Ser. No. 10/887,642, entitled SURGICAL SAGITTAL SAW AND METHOD OF USING SAME, filed 9 Jul. 2004, U.S. Patent Publication No. 2006/0009796, now U.S. Pat. No. 7,497,860, the contents of which are incorporated herein by reference.

Surgical sagittal saw 30 of this invention is assembled by seating the sagittal neck 50 inside the static collar 52. Two sets of ball bearings 188 and 189 disposed between neck 50 and collar 52 allow the neck to freely rotate relative to the collar. Ball bearings 188 seat in groove 78 within collar 52. The second set of ball bearings, bearings 189, seat in collar groove 80. When the neck 50 is fitted in collar 52, the ball bearings 189 in groove 80 press against tapered outer surface 92 of the collar.

A thrust ring 190 disposed over the distal end of the distal end of the stem 82 of the sagittal neck 50 press against the ball bearing seated in collar groove 78. Thrust ring 190 is slip-fitted around the sagittal neck stem 82. Thrust ring 190 has an outer circumferential surface 192 that is outwardly tapered. The thrust ring 190 is fitted over the sagittal neck so the surface 192 taper extends outwardly moving distal to proximally reardwardly along the ring. Outer surface 192 is the surface of the thrust ring that abuts ball bearings 188 seated in collar groove 78.

Wave springs 194 and lock nut 196 collectively function as a retaining assembly that hold the sagittal head and neck sub-assembly to collar 50 and that urge the sub-assembly proximally. The wave springs 194 and lock nut 196 also impose a small friction force on the free rotation of the neck 52. Plural wave springs 194 are stacked over the neck stem 82 behind the thrust ring. Lock nut 196 is screw secured to the neck threading 84 to press against the proximal most wave spring 194. The distal most wave spring 194 presses against the thrust ring 190 so as to push the thrust ring against ball bearings 188. Since thrust ring 190 is blocked from movement by ball bearings 188, wave springs 194 also urge lock nut 196 and, therefore, sagittal neck 52 proximally rearwardly. Wave springs 194 further impose a friction force on lock nut 196 and, therefore, sagittal neck 52 that inhibits rotation of these components. The friction force imposed by the wave springs can be overcome by manual force.

As a further consequence of neck 50 being urged proximally, the tapered surface 92 of the neck is urged against the distal ring of ball bearings 189. The abutment of neck tapered surface 92 against ball bearings 189 blocks sidewise wobble of the neck 50, and therefore head 48 relative to the fixed longitudinal axis of collar 52. Since the components neck outer surface 92 abuts are ball bearings 189, this contact does not appreciably adversely affect the rotation of the neck 50 in the collar 52.

An O-ring 197 is seated in groove sagittal neck groove 94. While not fully illustrated, it is understood that O-ring 197 presses against the adjacent inner surface of the collar 52 to provide a seal between the sagittal neck 50 and the collar.

Figure 19:
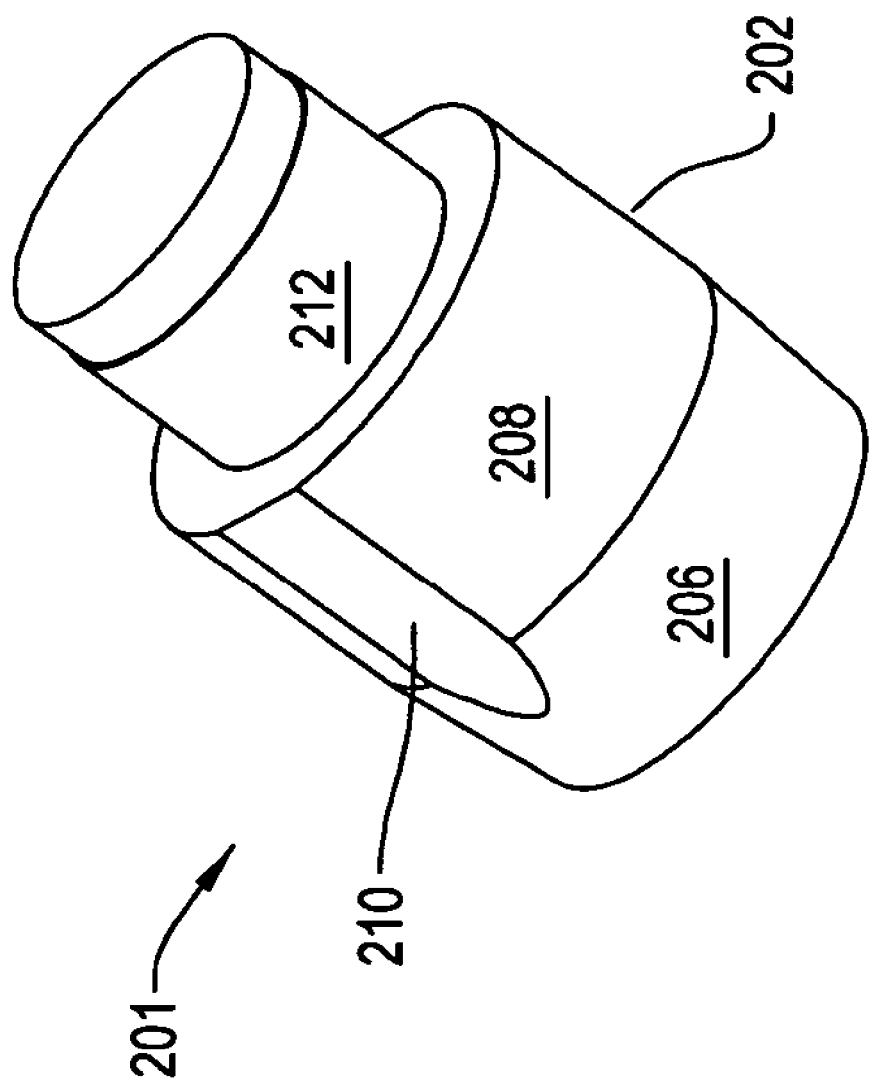
FIG. 19 is a perspective view of the lock pin.

Lock assembly 54 disposed inside the sagittal head 48 and the sagittal neck 50 releasably holds this assembly in a fixed angular orientation relative to the longitudinal center axis of collar 52. Lock assembly 54 includes a lock pin 201 that extends outwardly from the sagittal neck. The lock pin 201, seen best in FIG. 19, has a head 202. Lock pin head 202 has a nose 206 that forms the free end of the head. Nose 206 has a generally cylindrical body that is inwardly tapered. The taper of nose 206 is at the same general angle as the side faces 74 that define tabs 72 internal to collar 52. Extending from nose 206, pin head 202 is shaped to have a base 208. Base 208 has generally constant cross sectional diameter along the whole length of its length.

While nose and base 206 and 208, respectively, of the pin head 202 have generally curved cross sectional shaped, the pin head is further formed to have two diametrically opposed, longitudinally extending parallel flats 210 (one shown). Flats 210 extend the whole of the length of the head base 208 and partially along nose 206. Flats 210 thus provide pin head base 208 with an oval cross sectional profile. More particularly, lock pin 201 is shaped so that pin head base 208 can be slip fit in sagittal neck opening 102.

Extending from the top of head base 208, lock pin 201 is formed to have a stem 212. The stem 212 is cylindrical and has a diameter less than that of the pin head 202. Not identified is a taper at the end of stem 212 provided to facilitate assembly of the lock assembly 54.

Figure 20:
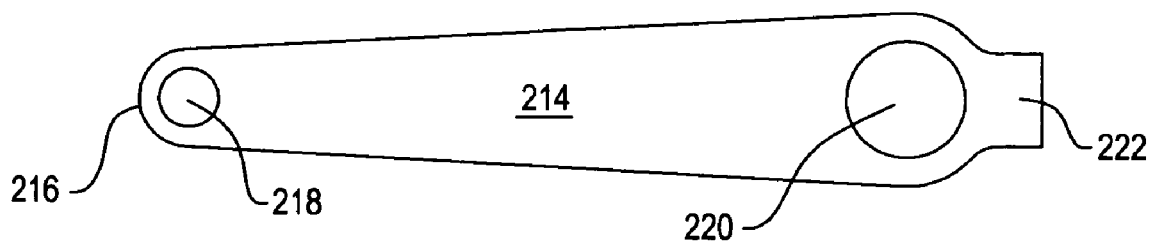
FIG. 20 is a plan view of the indexing link.

Normally, lock pin 201 seats in one of the slots 76 defined within the collar 52. An indexing link 214, seen best in FIG. 20, moves lock pin 201 in and out of slots 76 so the sagittal head and neck sub-assembly can be rotated. The indexing link 214 is generally in the form of an elongated, flat rod. At the distal end, index link has a curved face 216. Immediately proximal to the distal end, the link 214 is formed to have a first through opening 218. Extending rearwardly from the distal end, the indexing link is formed to have an increasing width. Immediately distal to the widest section of the link 214, the link has a second through opening 220. Lock pin stem 212 seats in opening 220.

Forward of the section of the indexing link 214 that defines opening 220, the link has a proximally extending tab 222. Tab 222 has a rectangular cross section and a width less than that of the adjacent section of the link in which opening 220 is formed. Tab 222 is the most proximal portion of the indexing link 214. The tab 222 is provided to facilitate disassembly of the saw 30. When saw 30 is assembled, the indexing link 214 extends through sagittal neck bore 98 into the proximal end bore 116 of the sagittal head 48.

Indexing link 214 is actuated by a release button 230 seen best in FIGS. 3 and 5. The release button 230 is generally cylindrical. Button 230 is nested in sagittal head bore 120. In the illustrated version of the invention, button 230 is formed with a reduced diameter base 231 that is disposed wholly in sagittal head bore 120. A cylindrical rod-like stem 232 extends from bore 120 through bore 124 and into sagittal head proximal end bore 116 to connect button 230 to the indexing link 214 for unitary motion. Not identified is the opening in the base 231 of button 230 in which stem 232 is seated or the opposed reduced diameter ends of the stem. While not illustrated, in some versions of the invention, the button base opening and stem 232 are formed with complementary threading to facilitate the screw securement of the stem to the release button 230. The reduced diameter ends of stem 232 facilitate and limit the fitting of the stem to the indexing link opening 218 and the release button 230.

A coil spring 234 extends around the portion of stem 232 disposed in sagittal head bore 120. Spring 234 is disposed at one end against the interior surface of the sagittal head 120 that defines bore 120. The opposed end of spring 234 seats against the annular step surface around release button stem 231. Since the interior surface of the sagittal head against which spring 234 seats in static, the spring pushes button 230 outwardly. By extension, this force pushes indexing link 214 and lock pin 202 outwardly. Spring 234 thus locks lock pin 202 in a collar slot 76. This engagement blocks rotation of the sagittal head and neck assembly around the longitudinal axis of collar 52.

Blade retention assembly 62 is now described by initial reference to FIGS. 3 and 5. The assembly 62 includes a back pin 240 fitted in bore 173. More particularly, pin 240 is seated in the closed end section of bore 173 and dimensioned to extend partially into blade slot 160. The exposed top surface of the back pin 240, the end surface in blade slot 60, is formed with a forward facing bevel, not identified. The bevel facilitates the loading and locking of a blade 32 in the blade slot 60. In some versions of the invention, the bevel may be eliminated. The section of the bore 173 open to the bottom face of blade mount head 156 facilitates insertion of the back pin 240.

Figure 27:
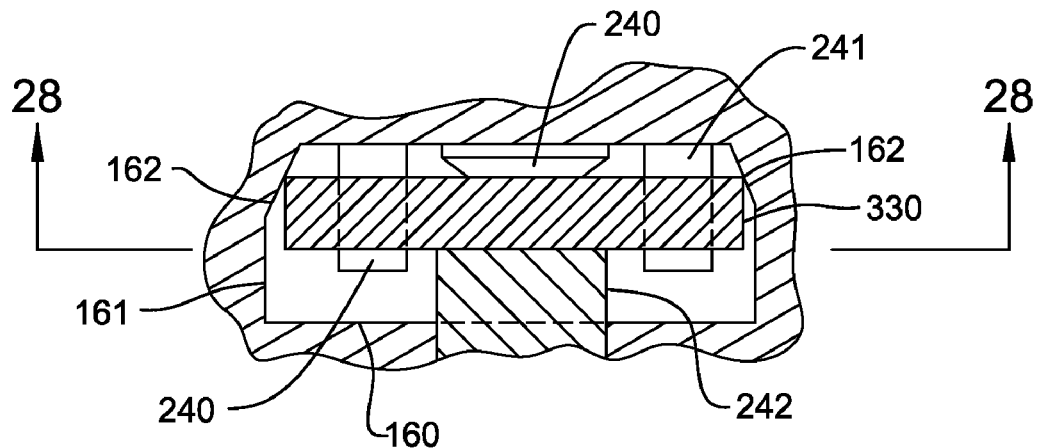
FIG. 27 is a cross sectional view illustrating the seating of the saw blade against the opposed side inner walls of the sagittal saw of this invention that define blade slot.
Figure 28:
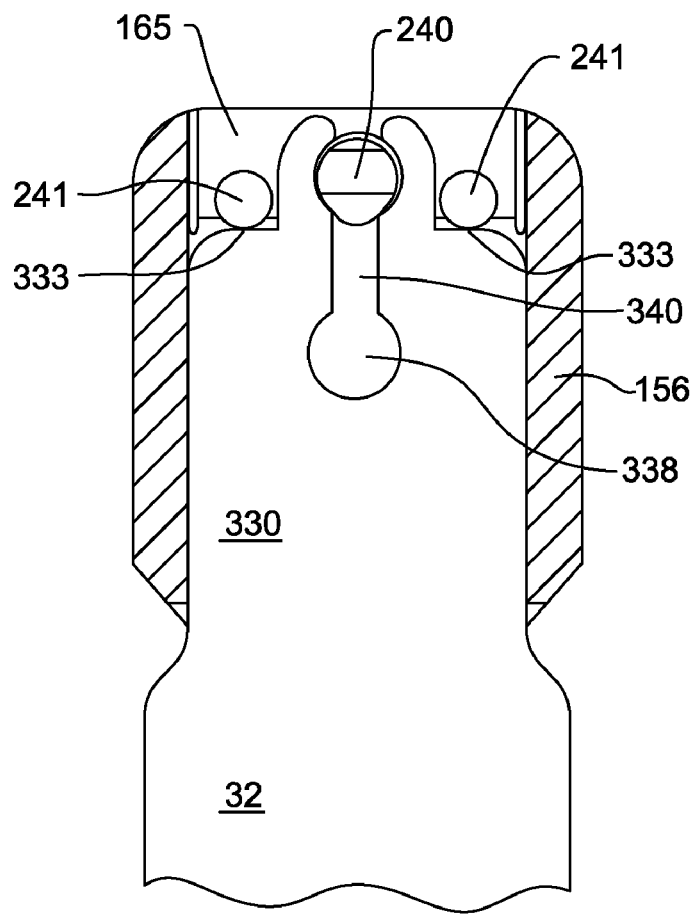
FIG. 28 is a projected view, looking upwardly along line 28-28 of FIG. 27, of how a saw blade is disposed against the interior surfaces of the blade mount head that define the top of the blade slot.

Also mounted to the blade mount head 156 so as to extend downwardly into the blade slot 60 are two blade pins 241, seen in FIGS. 27 and 28. Blade pins 241 are located slightly distally forward of the back pin 240. The center axes of the blade pins 241 are on a line that extends perpendicular to the longitudinal axis of the blade slot 60. The blade pins 241 have a diameter less than that of the back pin 240. While not seen in the drawings, it should be appreciated that the blade mount head is formed with two two-section bores similar to bore 173. Each of these bores receives a separate one of the insertion of one of the blade pins 241.

Blade retention assembly 62 also includes a sub-assembly for pushing the blade 32 against the opposed blade mount head interior surfaces 162 that define the blade slot 60 second section. This sub-assembly includes a flat head pin 242 seated in the blade mount bore 172. Pin 242 is generally cylindrical and is dimensioned to move freely in the blade mount bore 172.

Figure 21:
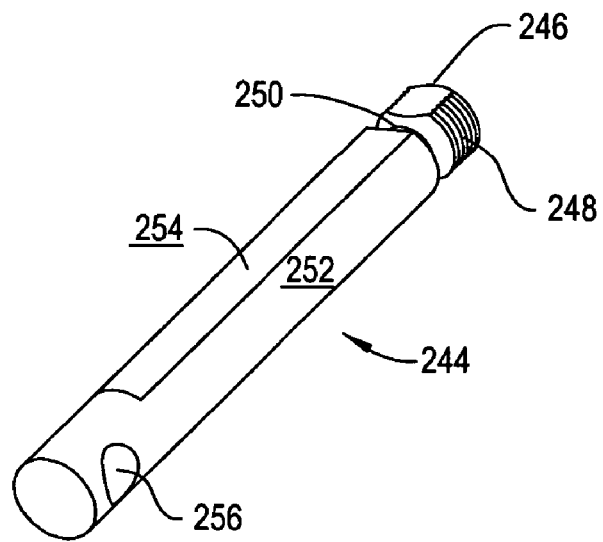
FIG. 21 is a perspective view of the actuating rod.

Flat head pin 242 is supported in the upper end of blade mount bore 172 by an actuating rod 244 also disposed in the bore. The actuating rod 244, best seen in FIG. 21, is in the form of a generally circular solid rod. Actuating rod 244 is shaped to have a head 246 the outer surface of which is provided with threading 248. A neck 250, with a diameter less than that of the head 248, is located immediately below the head. Below the neck 250, actuating rod 244 has a main body 252. The main body 252 has a diameter equal to that of the head 246.

While the actuating rod 244 has generally a circular cross sectional profile, the rod is formed to have two diametrically opposed longitudinally extending flats 254 (one shown). Flats 254 extend longitudinally along the complete length of the head 248 and along approximately three-fourths of the upper end of the main body 252. Owing to its recessed outer surface, the flats are not present in neck 250. Below the flats 254, the rod main body 252 is formed to have a laterally extending through hole 256. Hole 256 is formed so the longitudinal axis of the hole is perpendicular to the plane defined by the longitudinal axes of flats 254.

Flat head pin 242 is formed with an upwardly extending threaded through bore (not identified). Blade retention assembly 62 of this invention is assembled by screw securing rod head 246 in this bore of the flat head pin 242.

Figure 23:
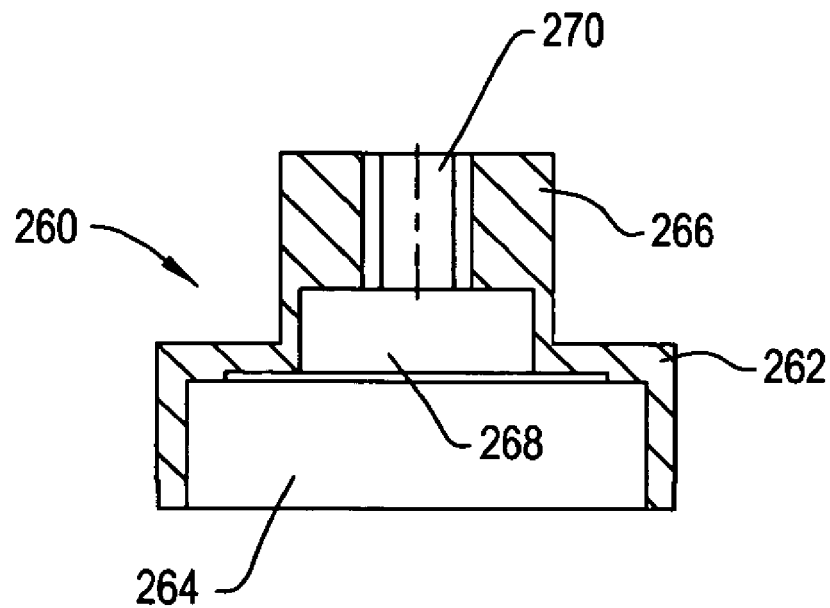
FIG. 23 is a cross sectional view of the bottom cap.
Figure 22:
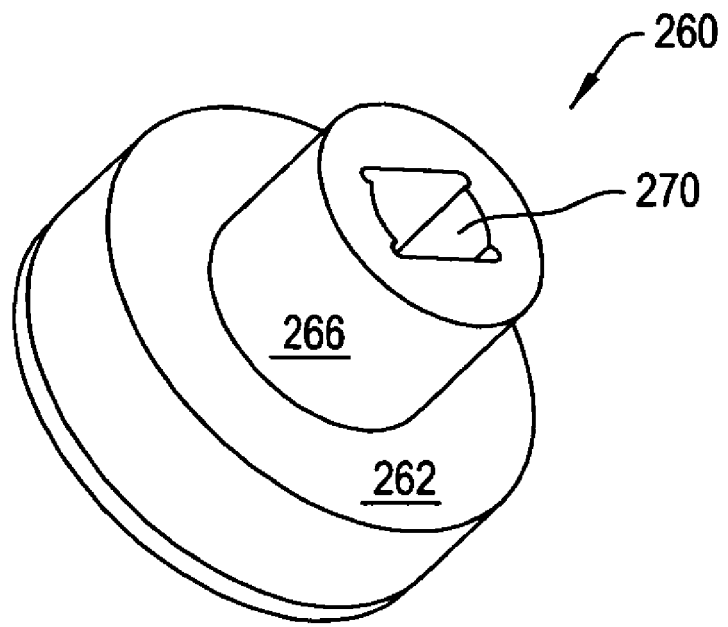
FIG. 22 is a perspective view of the bottom cap.

A bottom cap 260 centers the lower end of actuating rod 244 in the blade mount bore 172. The bottom cap 260, now described by reference to FIGS. 22 and 23, includes a circular base 262. Base 262 is shaped to define a circular bore 264 that extends upwardly from the end of the base. Bottom cap 260 includes a head 266 that extends coaxially upward from base 262. Head 266 has a circular cross sectional diameter. More particularly, head 266 is shaped to be nested in the open lower end of the blade mount bore 172 and be spaced away from the adjacent inner wall of the blade mount 56 so as to not affect the oscillation of the blade mount.

The bottom cap head 266 is formed to have a circular bore 268. Bore 268, which has a circular cross sectional profile, extends upwardly from the surface internal to the base 262 that defines the base of bore 264. Extending longitudinally upwardly from bore 268, cap head 266 is further formed to have an opening 270. Opening 270 extends from bore 268 to the top surface of the bottom cap head 266. Opening 270 is shaped to have a cross sectional profile similar to that of the portion of the actuating rod main body 252 subtended by flats 254. When saw 30 is assembled, this portion of the actuating rod 244 extends through bottom cap opening 270. Collectively, the actuating rod 244 and the bottom cap 260 are dimensioned so that the rod main body 252 can move through cap opening 270.

The bottom cap base 262 is disposed in fifth section 134 of sagittal head bore 122. Collectively, the components of the retention assembly 62 are dimensioned so that when the bottom cap 260 is so seated, the ring-shaped upwardly directed face of the base from which the cap head 266 extends is spaced longitudinally away from the bottom of the blade mount. This arrangement ensures that bottom cap 260, which is held static in the sagittal head 48, does not inhibit oscillation of the blade mount 56.

A finishing cap 274, also disposed in bore fifth section 134, holds the bottom cap 260 in the sagittal head bore. Finishing cap 274 is formed to have an annular skirt 276 that defines a circular void space 278. The finishing cap is dimensioned so that there is that the bottom cap is tightly fitted in void space 278. Threading, (not illustrated) on the interior surface of the sagittal head that defines bore section 134 and the outer surface of cap skirt 276 facilitate screw securement of the finishing cap 274 in the bore section.

Finishing cap 274 is further formed to have an opening 281 that extends through the center of the cap into void space 278.

Figure 25:
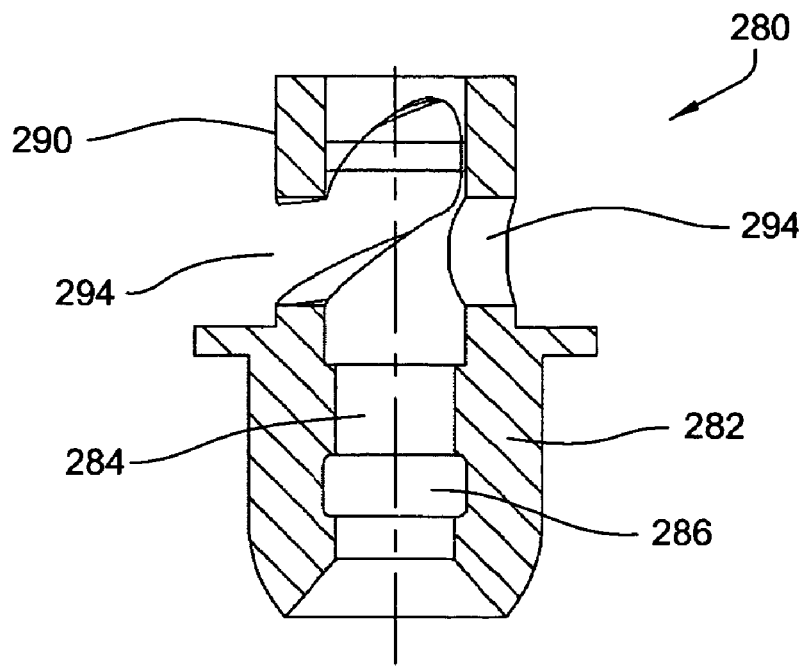
FIG. 25 is a cross sectional view of the barrel.
Figure 24:
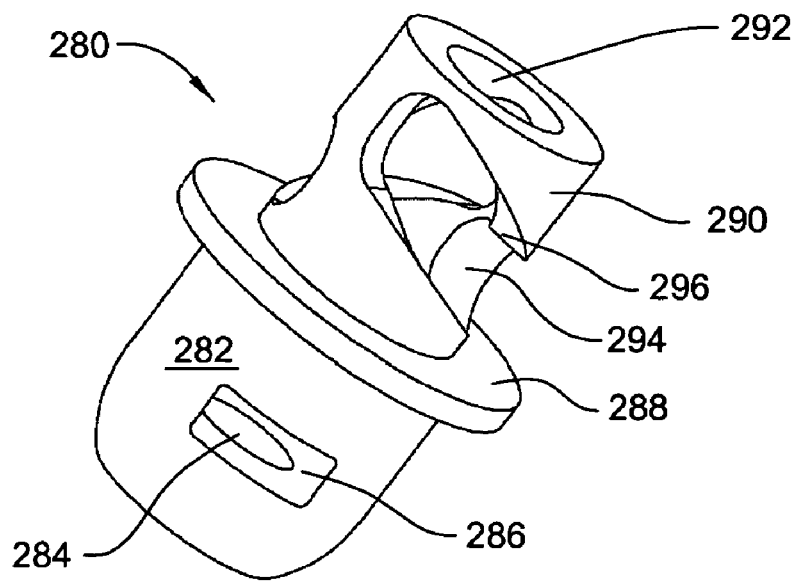
FIG. 24 is a perspective view of the barrel.

The end of the actuating rod main body 252 is fitted in a barrel 280 that is rotatably fitted in the bottom cap 260 and finishing cap 274. As illustrated in FIGS. 24 and 25, the barrel 280 has a head 282 (seen in the lower portions of Figures) with a circular cross sectional profile. The bottom end of the head 282 curves inwardly. Barrel head 282 is formed to have a longitudinally axially centered through bore 284. The barrel head 282 is further formed to have a slot 286 that extends laterally inwardly from the side of the head. Slot 286 extends across the whole of the diameter of the head and intersects bore 284.

Above head 282, barrel 280 has a collar 288 that extends radially outwardly and circumferentially around the base of the head. When saw 30 is assembled, barrel 280 is fitted in finishing cap 274 so that the barrel head 282 extends through the cap opening 281. Barrel collar 288 seats against the inner surface of the finishing cap 274 that defines opening 281 to hold the barrel 280 to the rest of the assembly. Collectively, the finishing cap 274 and the barrel 280 are formed so that the barrel head 282 can rotate in cap opening 281.

Barrel 280 also has a stem 290 that projects upwardly from collar 288. Stem 290 is circular in cross-sectional shape and has an outer diameter slightly less than that of the barrel head 282. A bore 292 extends axially through the stem 290 from the free end of stem, through collar 288, to head bore 284. Barrel stem 290 is further formed to have two diametrically opposed longitudinal slots 294. Each slot 294 extends in a helical pattern along the outer surface of the stem 290. Slots 294 open into barrel bore 292. Barrel stem 290 is further formed to define two detents 296 (one shown). Each detent 296 projects into an associated one of the slots 294 adjacent the lower end of the slot.

The barrel stem 290 is seated in bore 264 of the bottom cap base 262. A bearing assembly 298 rotatably centers the barrel stem 290 in the bottom cap base 262.

The circular bottom end of the actuating rod main body 252 is disposed in barrel bore 292. A pin 302 extends through hole 256 of actuating rod 244. The opposed ends of pin 302 project beyond the perimeter of actuating rod 244 and seat in the opposed barrel stem slots 294.

A lever 304 rotates the barrel 280. The lever has a planar body 308. A tab 310 extends outwardly from body 308. Tab 310 seats in barrel slot 286. A screw 312 that extend into the open end of barrel bore 284 and slot 286 screw secures the lever tab 310 to the barrel 280, (threaded opening in lever tab not shown).

Lever 304 is positioned so that body 308 is partially seated in and projects outwardly from sagittal head recess 115. A spring biased indexing pin 314 is mounted in a bore 315 in the lever body 308 to project outwardly towards the surface of the sagittal head 48 that defines the base of the recess. This surface is formed with a detent 318 (FIG. 5) in which the exposed end of pin 314 can seat. Detent 318 is positioned so that pin 314 seats in the detent when the lever 304 is rotated into a position to cause pin 302 to move to the upper ends of the barrel slots 294. As explained in detail below, when the lever 304 is so positioned, retention assembly 62 securely holds the blade 32 in the blade mount 56. The retention assembly 62 is considered to be in the "run" state.

A coil spring 320 is disposed in blade mount bore 172 around the actuating rod main body 252. The upper end of the bottom cap head 266 functions as the static surface against which spring 320 is seated. The opposed end of spring 320 is disposed against the undersurface of the flat head pin 242. Spring 320 thus imposes a force of the flat head pin 242 and the actuating rod 244 to urge the pin into the blade slot 60 and towards interior surfaces 166 and 167.

FIGS. 26A and 26B illustrate the proximal end 330 of the saw blade 32 used with surgical sagittal saw 30 of this invention. Blade 32 has opposed face surfaces 328 (one seen in FIG. 26A), that extend the width of the blade. The blade teeth, seen but not identified in FIG. 26A, extend along the distal end of the face surfaces 328. Opposed edge surfaces 329, one seen in FIG. 26B, extend between the face surfaces 328 and are thinner in width than the face surfaces 328. The face surfaces 328 and edge surfaces meet at corners, not identified. The blade proximal end 330 is the end inserted in blade slot 60. Extending proximally rearwardly from a rear edge 333 of blade proximal end 330 there are a pair of opposed tines 334. Tines 334 are shaped to define therebetween a circular opening 336. The illustrated blade proximal end 330 has a second opening 338 distal from opening 336. A slot 340 extends longitudinally distally through the blade proximal end between openings 336 and 338. Opening 338 and slot 340 are not relevant to this invention. It should also be recognized that blades having other geometric features may be employed with saw 30 of this invention. Further the geometry of the teeth at the distal end of the saw blade 32 are likewise not relevant to this invention.

As part of the process of preparing saw 30 of this invention for use, the sagittal head and neck assembly is rotated to the select angular orientation around the longitudinal axis of the handpiece head 38. This is accomplished by first depressing release button 230 inwardly. This action results in the like inward movement of indexing link 214 and, by extension, lock pin 201. The movement of the lock pin 201 retracts the pin out of the collar slot 76 in which the pin is seated. It should be appreciated that when these components of locking mechanism 54 are so positioned, pin 201 remains in sagittal neck opening 102; button 230 remains in sagittal head bore 122. The containment of the pin 201 and button 230 in their complementary defined openings 102 and 120, respectively, prevents lateral shifting of these components.

The sagittal head and neck subassembly is then rotated to the desired angular orientation. Thrust ring 190, the longitudinally static component against which wave springs 194 abut, is seated against a first ring of ball bearings 188. This arrangement means that, while wave springs 194 urge the head and neck sub assembly inwardly, this assembly imposes only a nominal friction force against the rotation of the neck. Moreover, the second ring of ball bearings 189 is disposed between the only interface between neck 50 and the surrounding static collar 50. Collectively, this means that once release button 230 is depressed, only nominal physical force is required to index the saw head 48.

Once this assembly is so positioned, the force imposed on the release button 230 is removed. Spring 234 causes the button 230 and therefore the indexing link 212 and lock pin 201 to return to their outwardly located positions. Lock pin 201 thus seats in a collar slot 76. This engagement of the lock pin 201 means the pin again holds the sagittal head and neck in a fixed angular position relative to the longitudinal axis of collar 52.

Normally, spring 320 urges flat head pin 242 into blade slot 60. At this time, blade retention assembly 62 is in the run state. Saw 30 is prepared for blade insertion by rotating lever 304 so that pin 314 moves away from head detent 318 and the lever arm is aligned with the longitudinal axis of the saw head 36, (the position of FIG. 2). This action results in rotation of barrel 280, around its longitudinal axis. The rotation of the barrel 280, in turn forces pin 302 to move downwardly, towards the barrel head 282. It should be appreciated that pin 302 moves longitudinally because bottom cap 260 prevents rotation of the actuating rod 244 and, therefore, pin 302. Consequently, the rotation of the barrel 280 results in the downward translational movement of pin 302 in barrel slots 294. This movement results in like downward movement of actuating rod 244 and flat head pin 242. When pin 302 seats in the base of barrel slots 294, detents 296 block the force of spring 320 from urging the subassembly upwardly. At this time, flat head pin 242 is retracted out of the blade slot 60. Retention assembly 62 is now in the blade load state.

Saw blade 32 is then inserted in the blade slot 60. In this process, the saw blade 32 is positioned so blade mount back pin 240 seats in blade proximal end opening 336. As seen in FIG. 28, blade base edges 333 abut the blade pins 241 to limit rearward insertion of the saw blade 32. This facilitates the seating of the back pin 240 in the blade proximal end opening 336.

Lever 304 is then rotated to return the retention assembly 62 to the run state, towards detent 318. Once the lever 304 is rotated to the point where its movement causes pin 302 to move beyond detents 296, spring 320 pushes the flat head pin 242 upwardly into the blade slot 60. Flat head pin 242 abuts the adjacent face surface 328 of the saw blade and pushes the saw blade proximal end 330 upwardly. The corners where the face surface 328 opposite pin 302 and edges surfaces 329 of the blade meet are pushed against the inwardly tapered blade mount inner surfaces 162. Thus, as seen by FIG. 27, the blade proximal end 330 is compression secured in the blade slot 60 by, on one side pin 242 and on the opposite side, at the opposed edges of the blade 32, by the blade mount inner surfaces 162. (In FIG. 27 dimensions are exaggerated for purposes of illustration.) Lever indexing pin 314 reseats in detent 318. Saw 30 and blade 32 are now ready for use.

The sagittal saw 30 of this invention is constructed so that when blade retention assembly is in the run state, the sides of blade base 330 are pressed against the opposed interior surfaces of the blade mount 60. This arrangement prevents the blade slap that would occur if the there when the saw is actuated and there were gaps between these components. The elimination of the blade slap likewise eliminates the noise generated by this contact.

Blade retention assembly 62 of this invention is further constructed so that back pin 240 locks the blade 30 against forward discharge from the blade mount 56.

Surgical saw 30 of this invention is further constructed to have a first assembly, a retention assembly, that holds the head and neck assembly to the rest of the saw and a second assembly, lock assembly 54, that selectively inhibits head and neck rotation. The retention assembly, while holding the head 48 and neck 50 to collar 52, only minimally inhibits the rotation of the neck 50 relative to the collar 52. This construction minimizes the amount of manual force required to index the sagittal head and neck into the desired angular position. Moreover, lock pin 201 seats relatively tightly against the adjacent slot-defining side walls 74 internal to collar 52. When the saw 30 is actuated, there is little, if any, side-to-side movement of the pin 201 against the collar tabs 72. The reduction in movement of pin 201 further keeps the amount of noise that is generated when the saw 30 of this invention is actuated to a minimum.

It should be appreciated that the foregoing description is directed to one specific version of the sagittal saw of this invention. Other versions of the saw may have features different from what has been described.

For example, there is no requirement that all saws constructed in accordance with this invention have both the blade retention assembly and indexing/index locking assembly as described.

Also, other versions of this invention may have features different from what has been described. For example, in alternative versions of the invention, the housing 34, the rotating saw head and complementary biasing assembly may be constructed so that biasing assembly urges the saw head outwardly relative to the saw head distal end opening in which the saw head is seated. Again, it should be appreciated that the saw is constructed so that when the saw head is so biased, a portion of the head is urged towards an adjacent surface of the housing 34.

In some versions of the invention, the lock pin that inhibits free rotation of the sagittal head and neck assembly may be arranged to move longitudinally instead of laterally.

Also, in some versions of the invention, the locking assembly that prevents rotation of the sagittal head and neck may be constructed so that the moving components (the lock pin) that inhibit rotation are moveable attached to the static saw housing 34. In these versions of the invention the sagittal neck is formed to define plural spaces in which the lock pin is selectively received.

Also, in some versions of the invention, the sagittal neck may be an exposed component that rotates over some type of static mounting boss integral with saw housing 34.

Other means may be employed to push or urge the blade base against the inwardly tapered walls of the blade slot. Thus, in some versions of the invention, the blade mount slot may be shaped so that the inwardly directed surfaces are located in the bottom of the blade slot. In these versions of the invention, the blade mount may have a moveable head. A biasing member or a clamping device selectively urges the head against the base so that the head urges the blade base downwardly against the tapered surfaces.

In some versions of the invention, biasing members such as springs 234 and 320 may not be need to, respectively, lock the head in a fixed angular orientation or hold the blade against the interior surfaces of the blade mount.

It should further be appreciated that the features of this invention may be incorporated in surgical saws other than sagittal saws. Thus, one or more features of the saw of this invention may be incorporated into a saw with a head that includes a drive mechanism for driving the saw blade in a reciprocating pattern, that is the blade moves back and forth in a path of travel on or parallel to the longitudinal axis along with the blade teeth are arranged.

Therefore, it is an object of the appended claims to cover all such modifications and variations that come within the true spirit and scope of this invention.

What is claimed is:

1. A surgical saw comprising:
   a housing having a distal end, said housing being formed so that there is an opening in the distal end and an interior wall that extends inwardly from the opening;
   a motor disposed in said housing;
   a head located adjacent the housing distal end opening and a neck integral with the head that extends into the housing distal end opening that is able to rotate within the housing distal end opening, the rotation of the neck resulting in the rotation of the head around an axis that extends from the housing distal end;
   a blade mount attached to said head to rotate with said head around the housing distal end, said blade mount having a retention assembly for removably holding a saw blade and being attached to said head to oscillate;
   a drive link that extends from said motor to said blade mount through said neck, said drive link configured to, upon actuation of said motor, oscillate said blade mount;
   a first ring of a plurality of bearings disposed around the interior wall of said housing so as to be located between the housing interior wall and said neck, said bearings able to move relative to both said housing and said neck and wherein said bearings extend circumferentially around said drive link;
   a retaining assembly located between said housing and said neck and around said drive link, said retaining assembly configured to urge said neck against the first ring of bearings and retain said neck in said housing wherein, when said neck is disposed against the first ring of bearings, said neck is able to rotate against the first ring of bearings and around the axis that extends from the housing distal end; and
   a lock assembly separate from said retaining assembly that extends between said housing and said neck, said lock assembly having a moveable lock pin that selectively engages in either one of said housing or said neck for releasably holding said neck in a fixed rotational position in the housing bore.

2. The surgical saw of claim 1, wherein one of said housing or said neck is formed with plural spaced apart spaces arranged in a circle, each space dimensioned to receive said lock pin.

3. The surgical saw of claim 1, wherein said lock assembly further includes: a link from which said lock pin extends; and a release button that extends from said link for displacing said link and said lock pin so that said lock pin can be selectively moved from a first position in which said lock pin engages said housing or said neck and a second position in which said lock pin is spaced from said housing or said neck.

4. The surgical saw of claim 1, wherein said lock assembly further includes a biasing member that is separate from said retaining assembly that holds said lock pin in an engaged position against said housing or said neck.

5. The surgical saw of claim 1, wherein said housing, said neck and said retaining assembly are arranged so that said retaining assembly urges said neck inwardly into said housing.

6. The surgical saw of claim 1, wherein said blade mount is attached to said head and said drive link is connected to said blade mount so that actuation of said blade mount by said drive link oscillates said blade mount in a sagittal pattern.

7. The surgical saw of claim 1, wherein:
- a second ring of a plurality of bearings is disposed around the interior wall of said housing so as to be between said housing and said neck, the second ring of bearings being spaced from the first ring of bearings, the bearings of the second ring of bearings being able to move relative to said housing; and
- said retaining assembly includes a ring disposed around said neck adjacent the second ring of bearings and said retaining assembly is configured to impose a force on said ring that results in said neck being pressed against the first ring of bearings and, simultaneously therewith, said ring being urged against the second ring of bearings.

8. The surgical saw of claim 1, wherein said retaining assembly includes a spring that imposes a force on said neck so as to urge said neck against the first ring of bearings.

9. A surgical sagittal saw, said saw including:
- a housing;
- a motor disposed in said housing;
- a blade mount moveably mounted to said housing, said blade mount having a slot for receiving a sagittal saw blade, the saw blade having opposed face surfaces that have a width thereacross and opposed edge surfaces located between the face surfaces, and corners where adjacent face and edge surfaces meet, the slot being defined by opposed top and bottom surfaces in said blade mount and opposed side walls in said blade mount that extend between the top and bottom surfaces, at least one of the side walls having a first surface that is spaced from the surface of the opposed side wall to define a slot first section having a width greater than the width of the face surfaces of the saw blade and a second surface that extends from the first surface and is tapered inwardly so as to have a section thereof that is spaced from the surface of the opposed side wall to define a slot second section having a width less than the width of the face surfaces of the saw blade;
- a retaining member mounted to said blade mount that extends into the slot second section for receiving a complementary retaining feature of the saw blade;
- a clamping assembly attached to said blade mount, said clamping assembly having:
  - a head moveably attached to said blade mount, said head having a run position in which said head is located adjacent one of the top or bottom interior surfaces of said blade mount so as to abut one of the face surfaces of the saw blade so as to urge the saw blade from the slot first slot section to the second slot section so that the blade corners distal to the head are pressed against the blade side walls and the blade is pressed towards the retaining member and a load position in which said head is retracted away from the top or bottom interior surface so that the blade can be removed from the blade mount slot; and
  - a manually actuated control member the moves the head between the run and load positions; and
- a drive mechanism that extends from said motor to said blade mount for oscillating said blade mount in a sagittal pattern.

10. The surgical saw of claim 9, wherein said blade mount is defined so that the opposed side walls each has a first surface, the first surfaces defining the slot first section and a second surface, the second surfaces being inwardly tapered inwardly toward each other so as to define the slot second section.

11. The surgical saw of claim 9, wherein said blade mount is further formed to have a plurality of walls that are angled relative to each other so as to define a void space contiguous with the slot second section.

12. The surgical saw of claim 9, wherein said clamping assembly includes a biasing member that normally urges said clamping assembly head towards the run position.

13. The surgical saw of claim 9, wherein said blade mount and said clamping assembly are attached to a saw head and said saw head is rotatably attached to said housing.

14. The surgical saw of claim 9, wherein said blade mount is shaped so that each slot-defining side wall has a first surface, the first surfaces being parallel to each other, the opposed first surfaces defining the slot first section, and a second surface, each second surface being tapered inwardly relative to the associated first surface, the opposed second surfaces defining the slot second section.

15. A surgical sagittal saw, said saw including:
- a housing;
- a motor disposed in said housing;
- a blade mount, said blade mount having:
  - a stem with a longitudinal axis that is mounted to said housing to oscillate about the longitudinal axis; and
  - a head integral with said stem so as to move with said stem, said blade mount head defining a slot that is open to receive a surgical sagittal saw blade, the slot being defined by: opposed top and bottom surfaces in said head; and opposed side walls in said head that extend between the top and bottom surfaces, at least one side wall formed to have first and second surfaces, the first surface being spaced apart from the opposed side wall so as to define a slot first section that has a width, the second surface tapering inwardly from the first surface so as to define a slot second section that has a width less than the width of the slot first section;
- a clamping assembly, said clamping assembly including:
  - a clamping head that is moveably mounted to said blade mount stem so as to have a run position in which said clamping head is adjacent one of the slot-defining top or bottom surfaces in said blade mount head so as to abut a sagittal saw blade and urge the blade into the slot second section so that opposed corners of the saw blade abut the opposed slot-defining side surfaces in the saw head and a load position in which said clamping head is spaced from the one of the slot-defining top or bottom surfaces in said blade mount head so that the sagittal saw blade can move into the slot first section; and
  - a manually actuated control member for moving the clamping head between the run and load positions; and
- a drive link connected between said motor and said blade mount stem configured to, upon actuation of said motor, oscillate said stem so that said blade mount displaces the saw blade in a sagittal motion.

16. The surgical saw of claim 15, wherein said blade mount head is shaped so that the opposed side walls in said head each have first and second surfaces, the first surfaces defining the slot first section, the second surfaces being inwardly tapered inwardly toward each other so as to define the slot second section.

17. The surgical saw of claim 15, wherein said blade mount head is further formed to have a plurality of walls that are angled relative to each other so as to define a void space contiguous with the slot second section.

18. The surgical saw of claim 15, wherein said clamping assembly includes a biasing member that normally urges said clamping head towards the slot second section.

19. The surgical saw of claim 15, wherein:
a retaining member is mounted to said blade mount head so as to extend into the slot second section and engage a complementary retaining feature of the saw blade; and
said clamping head is further configured to, when moved from the load position to the run position, displace the saw blade so that the saw blade retaining feature is moved into engagement with said blade mount retaining member.

20. The surgical saw of claim 15, wherein said blade mount is rotatably mounted to said housing to rotate around an axis that extends through said housing and said clamping assembly is mounted to said blade mount to rotate with said head.

21. A surgical saw, said saw including:
a housing, said housing having a distal end with an opening and an interior surface that defines a bore that extends proximally from the distal end opening;
a motor disposed in said housing;
a saw head located forward of the housing;
a neck that extends proximally from said saw head into the housing bore so as to rotate in the housing bore, the rotation of said neck resulting in a like rotation of said saw head;
a blade mount mounted to said saw head to rotate with the saw head, said blade mount being configured to removably receive a saw blade and being mounted to said saw head to oscillate around an axis that extends through the saw blade;
a drive link that extends from said motor, through said neck to said blade mount, said drive link configured to, upon actuation of said motor, oscillate said blade mount;
a first ring of bearings disposed around the housing interior surface so as to be located between the housing interior surface and said neck, the first ring of bearings comprising a plurality of individual bearings that are rotatable relative to both said housing and said neck and wherein the first ring of bearings extend around said drive link;
a second ring of bearings disposed around the housing interior surface so as to be located between the interior surface and said neck, said second ring of bearings being longitudinally spaced from the first ring of bearings along the housing interior surface and comprising a plurality of individual bearings that are rotatable relative to both said housing and said neck and wherein the second ring of bearings extend around said drive link;
a ring disposed over said neck so as to be rotatable relative to said neck, said ring located adjacent the second ring of bearings;
a retaining assembly located between said neck and said housing and that is located adjacent said ring, said retaining assembly configured to impose force on both said neck and said ring so as to simultaneously urge said neck against the first ring of bearings and said ring against the second ring of bearings so as to hold said neck in said housing;
a lock pin moveably mounted to one of said housing or said neck to releasably engage the other of said neck or said housing so that when said lock pin is so engaged, said lock blocks rotation of said neck in the housing bore.

22. The surgical saw of claim 21, wherein said blade mount is rotatably mounted in said saw head and said blade mount and said drive link are collectively configured so that, when said motor is actuated, said blade mount oscillates in a sagittal pattern.

23. The surgical saw of claim 21, wherein said retaining assembly is configured to impose a force on said neck so as to urge said saw head towards said housing.

24. The surgical saw of claim 21, wherein:
said housing is formed to define a plurality of arcuately spaced apart slots, each said slot being dimensioned to receive said lock pin; and
said lock pin is mounted to said neck to rotate with said neck and positioned so as to be selectively seated in the slots defined by said housing.

25. The surgical saw of claim 21, wherein:
said blade mount is formed with a plurality of interior walls that define a slot for receiving the saw blade; and
said blade mount includes a clamping member that is moveably mounted to said blade mount so as to releasably urge the saw blade against one of the interior walls of the blade mount so as to cause the saw blade to be compression secured between the blade mount interior wall and said clamping member.

26. The surgical saw of claim 21, wherein:
said retaining assembly includes a first biasing member that extends between said neck and said ring that imposes a force on both said neck and said ring to urge said neck against the first ring of bearings and said ring against the second ring of bearings; and
said lock assembly includes a second biasing member separate from said first biasing member that holds said lock pin in an engaged position against said housing or said neck.

27. The surgical saw of claim 9, wherein:
said blade mount includes: a head in which the blade mount slot is formed and a trunk that extends from said head, said trunk being moveably mounted to said housing and having a bore that opens into the blade mount slot;
said drive mechanism is connected to said blade mount trunk; and
said clamping assembly includes a rod to which said clamping assembly head is connected, said rod being moveably mounted in the bore of said blade mount trunk; and
said clamping assembly control member is connected to said clamping assembly rod so as to move said rod within said blade mount trunk, the movement of said rod moving said clamping assembly head between the run and load positions.

28. The surgical saw of claim 15, wherein said blade mount stem has a plurality of sections with different outer diameters.

29. The surgical saw of claim 15, wherein:
said blade mount stem includes a bore that opens into the slot in said blade mount head;
said clamping assembly includes a rod to which said clamping head is connected, said rod being moveably mounted in the bore of said blade mount stem; and
said clamping assembly control member is connected to said clamping assembly rod so as to move said rod in said blade mount stem, the movement of said rod moving said clamping head between the run and load positions.

30. The surgical saw of claim 29, further including a spring disposed in the bore of said blade mount stem, said spring positioned to press against said clamping assembly head to urge said clamping head into the run position.

* * * * *